United States Patent
Zhang et al.

(10) Patent No.: US 10,335,146 B2
(45) Date of Patent: Jul. 2, 2019

(54) SURGICAL FASTENER APPLYING APPARATUS, KITS AND METHODS FOR ENDOSCOPIC PROCEDURES

(71) Applicant: Covidien LP, Mansfield, MA (US)

(72) Inventors: Jiangfeng Zhang, Shanghai (CN); Shunhong Xu, Shanghai (CN); Xiliang Zhang, Shanghai (CN)

(73) Assignee: Coviden LP, Mansfield, MA (US)

( * ) Notice: Subject to any disclaimer, the term of this patent is extended or adjusted under 35 U.S.C. 154(b) by 346 days.

(21) Appl. No.: 15/129,143

(22) PCT Filed: Apr. 2, 2014

(86) PCT No.: PCT/CN2014/074583
§ 371 (c)(1),
(2) Date: Sep. 26, 2016

(87) PCT Pub. No.: WO2015/149292
PCT Pub. Date: Oct. 8, 2015

(65) Prior Publication Data
US 2017/0128068 A1    May 11, 2017

(51) Int. Cl.
*A61F 2/00*    (2006.01)
*A61B 17/00*    (2006.01)
(Continued)

(52) U.S. Cl.
CPC .. *A61B 17/07207* (2013.01); *A61B 17/00234* (2013.01); *A61B 17/064* (2013.01);
(Continued)

(58) Field of Classification Search
CPC .... A61B 2017/0648; A61B 2017/0649; A61B 2017/0647; A61B 2017/2923;
(Continued)

(56) References Cited

U.S. PATENT DOCUMENTS 3,596,528 A    8/1971    Dittrich et al.
3,866,510 A    2/1975    Eibes et al.
(Continued)

FOREIGN PATENT DOCUMENTS

CA    2999907 A1 *    5/2017    ......... A61B 17/1285
CA    3009420 A1 *    7/2017    ......... A61B 17/1285
(Continued)

OTHER PUBLICATIONS

European Office Action corresponding to Patent Application EP 14 15 89465 dated Apr. 26, 2018.
(Continued)

*Primary Examiner* — Hemant Desai
*Assistant Examiner* — Veronica Martin

(57) ABSTRACT

An endoscopic surgical device is provided and includes a handle assembly including a handle housing and a trigger operatively connected to the handle housing, and a drive mechanism actuatable by the trigger; and an endoscopic assembly selectively connectable to the handle assembly. The endoscopic assembly includes an outer tube defining a lumen therethrough and having a helical thread disposed within the lumen thereof; an inner tube rotatably supported in the outer tube and being operatively connectable to the drive mechanism, the inner tube defining a splined distal end, wherein the splined distal end of the inner tube is defined by a pair of opposed longitudinally extending tines and a pair of opposed longitudinally extending channels; and a plurality of surgical anchors loaded in the splined distal end of the inner tube.

10 Claims, 26 Drawing Sheets

(51) Int. Cl.
*A61B 17/29* (2006.01)
*A61B 17/064* (2006.01)
*A61B 17/068* (2006.01)
*A61B 17/072* (2006.01)

(52) U.S. Cl.
CPC .......... *A61B 17/068* (2013.01); *A61F 2/0063* (2013.01); *A61B 2017/0046* (2013.01); *A61B 2017/00407* (2013.01); *A61B 2017/00477* (2013.01); *A61B 2017/0648* (2013.01); *A61B 2017/2903* (2013.01); *A61B 2017/2923* (2013.01); *A61B 2017/2946* (2013.01); *A61F 2002/0072* (2013.01)

(58) Field of Classification Search
CPC ...... A61B 2017/0409; A61B 2017/068; A61B 2017/064; A61B 17/07207; A61B 17/00234; A61B 17/064; A61B 17/068; A61F 2/0063
See application file for complete search history.

(56) References Cited

U.S. PATENT DOCUMENTS

| | | |
|---|---|---|
| 4,350,491 A | 9/1982 | Steuer |
| 4,884,572 A | 12/1989 | Bays et al. |
| 5,085,661 A | 2/1992 | Moss |
| 5,171,247 A | 12/1992 | Hughett et al. |
| 5,171,249 A | 12/1992 | Stefanchik et al. |
| 5,176,306 A | 1/1993 | Heimerl et al. |
| 5,207,697 A * | 5/1993 | Carusillo ........... A61B 17/1626 320/115 |
| 5,228,256 A | 7/1993 | Dreveny |
| 5,236,563 A | 8/1993 | Loh |
| 5,246,441 A | 9/1993 | Ross et al. |
| 5,246,450 A | 9/1993 | Thornton et al. |
| 5,312,023 A | 5/1994 | Green et al. |
| 5,330,487 A | 7/1994 | Thornton et al. |
| 5,344,061 A | 9/1994 | Crainich |
| 5,356,064 A | 10/1994 | Green et al. |
| 5,382,254 A | 1/1995 | McGarry et al. |
| 5,398,861 A | 3/1995 | Green |
| 5,403,327 A | 4/1995 | Thornton et al. |
| 5,433,721 A | 7/1995 | Hooven et al. |
| 5,439,468 A | 8/1995 | Schulze et al. |
| 5,466,243 A | 11/1995 | Schmieding et al. |
| 5,467,911 A | 11/1995 | Tsuruta et al. |
| 5,474,566 A | 12/1995 | Alesi et al. |
| 5,474,567 A | 12/1995 | Stefanchik et al. |
| 5,522,844 A | 6/1996 | Johnson |
| 5,527,319 A | 6/1996 | Green et al. |
| 5,553,765 A | 9/1996 | Knodel et al. |
| 5,562,685 A | 10/1996 | Mollenauer et al. |
| 5,564,615 A | 10/1996 | Bishop et al. |
| 5,582,615 A | 12/1996 | Foshee et al. |
| 5,582,616 A | 12/1996 | Bolduc et al. |
| 5,584,425 A | 12/1996 | Savage et al. |
| 5,588,581 A | 12/1996 | Conlon et al. |
| 5,601,571 A | 2/1997 | Moss |
| 5,601,573 A | 2/1997 | Fogelberg et al. |
| 5,626,613 A | 5/1997 | Schmieding |
| 5,628,752 A | 5/1997 | Asnis et al. |
| 5,649,931 A | 7/1997 | Bryant et al. |
| 5,662,662 A | 9/1997 | Bishop et al. |
| 5,681,330 A | 10/1997 | Hughett et al. |
| 5,683,401 A | 11/1997 | Schmieding et al. |
| 5,685,474 A | 11/1997 | Seeber |
| 5,697,935 A | 12/1997 | Moran et al. |
| 5,709,692 A | 1/1998 | Mollenauer et al. |
| 5,730,744 A | 3/1998 | Justin et al. |
| 5,732,806 A | 3/1998 | Foshee et al. |
| 5,735,854 A * | 4/1998 | Caron ............... A61B 17/8875 606/104 |
| 5,741,268 A | 4/1998 | Schutz |
| 5,762,255 A | 6/1998 | Chrisman et al. |
| 5,782,844 A | 7/1998 | Yoon et al. |
| 5,810,882 A | 9/1998 | Bolduc et al. |
| 5,811,552 A | 9/1998 | Nishikata et al. |
| 5,824,008 A | 10/1998 | Bolduc et al. |
| 5,830,221 A | 11/1998 | Stein et al. |
| 5,843,087 A | 12/1998 | Jensen et al. |
| 5,897,564 A | 4/1999 | Schulze et al. |
| 5,904,693 A * | 5/1999 | Dicesare ........... A61B 17/1285 227/901 |
| 5,910,105 A | 6/1999 | Swain et al. |
| 5,911,722 A | 6/1999 | Adler et al. |
| 5,928,244 A * | 7/1999 | Tovey ................. A61F 2/0805 606/104 |
| 5,928,252 A | 7/1999 | Steadman et al. |
| 5,931,844 A | 8/1999 | Thompson et al. |
| 5,941,439 A | 8/1999 | Kammerer et al. |
| 5,954,259 A * | 9/1999 | Viola ............... A61B 17/07207 227/176.1 |
| 5,961,524 A | 10/1999 | Crombie |
| 5,964,772 A | 10/1999 | Bolduc et al. |
| 5,976,160 A | 11/1999 | Crainich |
| 5,997,552 A | 12/1999 | Person et al. |
| 6,010,513 A | 1/2000 | Tormala et al. |
| 6,013,991 A | 1/2000 | Philipp |
| 6,039,753 A | 3/2000 | Meislin |
| 6,074,395 A | 6/2000 | Trott et al. |
| 6,099,537 A * | 8/2000 | Sugai ................ A61B 17/0684 606/143 |
| 6,126,670 A | 10/2000 | Walker et al. |
| 6,132,435 A | 10/2000 | Young |
| 6,146,387 A | 11/2000 | Trott et al. |
| 6,183,479 B1 | 2/2001 | Tormala et al. |
| 6,228,098 B1 | 5/2001 | Kayan et al. |
| 6,235,058 B1 | 5/2001 | Huene |
| 6,241,736 B1 | 6/2001 | Sater et al. |
| 6,261,302 B1 | 7/2001 | Voegele et al. |
| 6,296,656 B1 | 10/2001 | Bolduc et al. |
| 6,330,964 B1 | 12/2001 | Kayan et al. |
| 6,387,113 B1 | 5/2002 | Hawkins et al. |
| 6,402,757 B1 | 6/2002 | Moore, III et al. |
| 6,425,900 B1 | 7/2002 | Knodel et al. |
| 6,439,446 B1 | 8/2002 | Perry et al. |
| 6,440,136 B1 | 8/2002 | Gambale et al. |
| 6,450,391 B1 | 9/2002 | Kayan et al. |
| 6,457,625 B1 | 10/2002 | Tormala et al. |
| 6,551,333 B2 | 4/2003 | Kuhns et al. |
| 6,562,051 B1 | 5/2003 | Bolduc et al. |
| 6,572,626 B1 | 6/2003 | Knodel et al. |
| 6,589,249 B2 | 7/2003 | Sater et al. |
| 6,592,593 B1 | 7/2003 | Parodi et al. |
| 6,626,916 B1 | 9/2003 | Yeung et al. |
| 6,632,228 B2 | 10/2003 | Fortier et al. |
| 6,652,538 B2 | 11/2003 | Kayan et al. |
| 6,663,656 B2 | 12/2003 | Schmieding et al. |
| 6,666,854 B1 | 12/2003 | Lange |
| 6,695,867 B2 | 2/2004 | Ginn et al. |
| 6,733,506 B1 | 5/2004 | McDevitt et al. |
| 6,743,240 B2 | 6/2004 | Smith et al. |
| 6,749,621 B2 | 6/2004 | Pantages et al. |
| 6,755,836 B1 | 6/2004 | Lewis |
| 6,773,438 B1 | 8/2004 | Knodel et al. |
| 6,800,081 B2 | 10/2004 | Parodi |
| 6,824,548 B2 | 11/2004 | Smith et al. |
| 6,837,893 B2 | 1/2005 | Miller |
| 6,840,943 B2 | 1/2005 | Kennefick et al. |
| 6,843,794 B2 | 1/2005 | Sixto, Jr. et al. |
| 6,869,435 B2 * | 3/2005 | Blake, III ........... A61B 17/1285 606/143 |
| 6,884,248 B2 | 4/2005 | Bolduc et al. |
| 6,887,244 B1 | 5/2005 | Walker et al. |
| 6,893,446 B2 | 5/2005 | Sater et al. |
| 6,905,057 B2 | 6/2005 | Swayze et al. |
| 6,929,661 B2 | 8/2005 | Bolduc et al. |
| 6,942,674 B2 | 9/2005 | Belef et al. |
| 6,945,979 B2 | 9/2005 | Kortenbach et al. |
| 6,960,217 B2 | 11/2005 | Bolduc |
| 6,966,919 B2 | 11/2005 | Sixto, Jr. et al. |
| 6,988,650 B2 | 1/2006 | Schwemberger et al. |

(56) References Cited

U.S. PATENT DOCUMENTS

| | | |
|---|---|---|
| 7,000,819 B2 | 2/2006 | Swayze et al. |
| 7,128,754 B2 | 10/2006 | Bolduc |
| 7,147,657 B2 | 12/2006 | Chiang et al. |
| 7,204,847 B1 | 4/2007 | Gambale |
| 7,261,716 B2 | 8/2007 | Strobel et al. |
| 7,491,232 B2 | 2/2009 | Bolduc et al. |
| 7,544,198 B2 | 6/2009 | Parodi |
| 7,591,842 B2 | 9/2009 | Parodi |
| 7,637,932 B2 | 12/2009 | Bolduc et al. |
| 7,670,362 B2 | 3/2010 | Zergiebel |
| 7,758,612 B2 | 7/2010 | Shipp |
| 7,823,267 B2 | 11/2010 | Bolduc |
| 7,828,838 B2 | 11/2010 | Bolduc et al. |
| 7,862,573 B2 | 1/2011 | Darois et al. |
| 7,867,252 B2 | 1/2011 | Criscuolo et al. |
| 7,905,890 B2 | 3/2011 | Whitfield et al. |
| 7,931,660 B2 | 4/2011 | Aranyi et al. |
| 7,959,663 B2 | 6/2011 | Bolduc |
| 7,959,670 B2 | 6/2011 | Bolduc |
| 8,002,811 B2 | 8/2011 | Corradi et al. |
| 8,034,076 B2 | 10/2011 | Criscuolo et al. |
| 8,075,570 B2 | 12/2011 | Bolduc et al. |
| 8,083,752 B2 | 12/2011 | Bolduc |
| 8,087,142 B2 | 1/2012 | Levin et al. |
| 8,092,519 B2 | 1/2012 | Bolduc |
| 8,114,099 B2 | 2/2012 | Shipp |
| 8,114,101 B2 | 2/2012 | Criscuolo et al. |
| 8,216,272 B2 | 7/2012 | Shipp |
| 8,231,639 B2 | 7/2012 | Bolduc et al. |
| 8,282,670 B2 | 10/2012 | Shipp |
| 8,292,933 B2 | 10/2012 | Zergiebel |
| 8,323,314 B2 | 12/2012 | Blier |
| 8,328,823 B2 | 12/2012 | Aranyi et al. |
| 8,343,176 B2 | 1/2013 | Criscuolo et al. |
| 8,343,184 B2 | 1/2013 | Blier |
| 8,382,778 B2 | 2/2013 | Criscuolo et al. |
| 8,414,627 B2 | 4/2013 | Corradi et al. |
| 8,465,520 B2 | 6/2013 | Blier |
| 8,474,679 B2 | 7/2013 | Felix |
| 8,506,475 B2 * | 8/2013 | Brannon ............ A61B 1/00154 600/104 |
| 8,579,919 B2 | 11/2013 | Bolduc et al. |
| 8,579,920 B2 | 11/2013 | Nering et al. |
| 8,597,311 B2 | 12/2013 | Criscuolo et al. |
| 8,685,044 B2 | 4/2014 | Bolduc et al. |
| 8,690,897 B2 | 4/2014 | Bolduc |
| 8,728,102 B2 | 5/2014 | Criscuolo et al. |
| 8,728,120 B2 | 5/2014 | Blier |
| 8,777,969 B2 | 7/2014 | Kayan |
| 8,821,514 B2 | 9/2014 | Aranyi |
| 8,821,522 B2 | 9/2014 | Criscuolo et al. |
| 8,821,557 B2 | 9/2014 | Corradi et al. |
| 8,852,215 B2 | 10/2014 | Criscuolo et al. |
| 8,875,971 B2 * | 11/2014 | Hall ................ A61B 17/07207 227/175.2 |
| 8,920,439 B2 | 12/2014 | Cardinale et al. |
| 8,926,637 B2 | 1/2015 | Zergiebel |
| 9,017,345 B2 * | 4/2015 | Taylor ................ A61B 17/068 606/142 |
| 9,023,065 B2 | 5/2015 | Bolduc et al. |
| 9,028,495 B2 | 5/2015 | Mueller et al. |
| 9,138,225 B2 * | 9/2015 | Huang ................ A61B 17/068 |
| 9,186,138 B2 | 11/2015 | Corradi et al. |
| 9,259,221 B2 | 2/2016 | Zergiebel |
| 9,282,961 B2 | 3/2016 | Whitman et al. |
| 9,332,983 B2 * | 5/2016 | Shipp ................ A61B 17/064 |
| 9,351,728 B2 * | 5/2016 | Sniffin ................ A61B 17/064 |
| 9,351,733 B2 | 5/2016 | Fischvogt |
| 9,358,004 B2 * | 6/2016 | Sniffin ................ A61B 17/068 |
| 9,358,010 B2 * | 6/2016 | Wenchell ............ A61B 17/10 |
| 9,364,274 B2 | 6/2016 | Zergiebel |
| 9,402,623 B2 | 8/2016 | Kayan |
| 9,486,218 B2 | 11/2016 | Criscuolo et al. |
| 9,526,498 B2 | 12/2016 | Reed |
| 9,655,621 B2 * | 5/2017 | Abuzaina ............ A61B 17/064 |
| 9,668,730 B2 * | 6/2017 | Sniffin ................ A61B 17/068 |
| 9,801,633 B2 | 10/2017 | Sholev et al. |
| 9,867,620 B2 | 1/2018 | Fischvogt et al. |
| 9,987,010 B2 | 6/2018 | Zergiebel |
| 10,070,860 B2 | 9/2018 | Zergiebel |
| 2002/0087170 A1* | 7/2002 | Kuhns ................ A61B 17/064 606/143 |
| 2003/0009441 A1* | 1/2003 | Holsten ............. A61B 17/068 |
| 2003/0114839 A1 | 6/2003 | Looper et al. |
| 2004/0092937 A1 | 5/2004 | Criscuolo et al. |
| 2004/0111089 A1 | 6/2004 | Stevens et al. |
| 2004/0127916 A1 | 7/2004 | Bolduc et al. |
| 2004/0181222 A1 | 9/2004 | Culbert et al. |
| 2004/0193217 A1 | 9/2004 | Lubbers et al. |
| 2004/0243139 A1* | 12/2004 | Lewis ................ A61B 17/862 606/104 |
| 2006/0129152 A1 | 6/2006 | Shipp |
| 2006/0129154 A1 | 6/2006 | Shipp |
| 2007/0038220 A1* | 2/2007 | Shipp ................ A61B 17/064 606/326 |
| 2007/0088390 A1 | 4/2007 | Paz et al. |
| 2007/0162030 A1 | 7/2007 | Aranyi et al. |
| 2008/0086154 A1* | 4/2008 | Taylor ................ A61B 17/068 606/142 |
| 2008/0097523 A1 | 4/2008 | Bolduc et al. |
| 2008/0147113 A1 | 6/2008 | Nobis et al. |
| 2008/0188868 A1 | 8/2008 | Weitzner et al. |
| 2008/0243106 A1 | 10/2008 | Coe et al. |
| 2008/0281336 A1* | 11/2008 | Zergiebel ............ A61B 17/068 606/142 |
| 2008/0281353 A1* | 11/2008 | Aranyi ................ A61B 17/064 606/219 |
| 2008/0312687 A1 | 12/2008 | Blier |
| 2009/0112234 A1 | 4/2009 | Crainich et al. |
| 2009/0118776 A1 | 5/2009 | Kelsch et al. |
| 2009/0188965 A1 | 7/2009 | Levin et al. |
| 2010/0030262 A1* | 2/2010 | McLean ............ A61B 17/0401 606/232 |
| 2010/0270354 A1 | 10/2010 | Rimer et al. |
| 2010/0292710 A1 | 11/2010 | Daniel et al. |
| 2010/0292713 A1* | 11/2010 | Cohn ................ A61B 17/1285 606/143 |
| 2010/0292715 A1 | 11/2010 | Nering et al. |
| 2011/0022065 A1 | 1/2011 | Shipp |
| 2011/0042441 A1 | 2/2011 | Shelton, IV et al. |
| 2011/0060349 A1 | 3/2011 | Cheng et al. |
| 2011/0071578 A1 | 3/2011 | Colesanti et al. |
| 2011/0079627 A1 | 4/2011 | Cardinale et al. |
| 2011/0087240 A1* | 4/2011 | Shipp ................ A61B 17/064 606/139 |
| 2011/0295269 A1 | 12/2011 | Swensgard et al. |
| 2011/0295282 A1 | 12/2011 | Glick et al. |
| 2012/0059397 A1 | 3/2012 | Criscuolo et al. |
| 2012/0109157 A1 | 5/2012 | Criscuolo et al. |
| 2013/0110088 A1 | 5/2013 | Wenchell |
| 2013/0197591 A1 | 8/2013 | Corradi et al. |
| 2014/0114329 A1 | 4/2014 | Zergiebel |
| 2014/0200587 A1 | 7/2014 | Pompee et al. |
| 2014/0243855 A1 | 8/2014 | Sholev et al. |
| 2014/0276967 A1 | 9/2014 | Fischvogt et al. |
| 2014/0276969 A1 | 9/2014 | Wenchell et al. |
| 2014/0276972 A1 | 9/2014 | Abuzaina et al. |
| 2014/0316446 A1 | 10/2014 | Kayan |
| 2015/0001272 A1 | 1/2015 | Sniffin et al. |
| 2015/0005748 A1 | 1/2015 | Sniffin et al. |
| 2015/0005788 A1* | 1/2015 | Sniffin ................ A61B 17/064 606/139 |
| 2015/0005789 A1* | 1/2015 | Sniffin ................ A61B 17/068 606/139 |
| 2015/0018847 A1 | 1/2015 | Criscuolo et al. |
| 2015/0032130 A1 | 1/2015 | Russo |
| 2015/0080911 A1* | 3/2015 | Reed ................ A61B 17/068 606/139 |
| 2015/0133970 A1 | 5/2015 | Ranucci et al. |
| 2015/0133971 A1 | 5/2015 | Ranucci et al. |
| 2015/0133972 A1 | 5/2015 | Ranucci et al. |
| 2015/0150558 A1 | 6/2015 | Zergiebel |
| 2015/0327859 A1 | 11/2015 | Bolduc |

(56) References Cited

U.S. PATENT DOCUMENTS

| | | |
|---|---|---|
| 2016/0007991 A1 | 1/2016 | Bolduc |
| 2016/0007996 A1 | 1/2016 | Bolduc |
| 2016/0066971 A1 | 3/2016 | Corradi et al. |
| 2016/0074034 A1 | 3/2016 | Shipp |
| 2016/0135807 A1 | 5/2016 | Zergiebel |
| 2016/0166255 A1* | 6/2016 | Fischvogt ............ A61B 17/064 606/139 |
| 2016/0249912 A1 | 9/2016 | Fischvogt |
| 2016/0270778 A1 | 9/2016 | Zergiebel |
| 2016/0270835 A1 | 9/2016 | Reed |
| 2016/0278766 A1 | 9/2016 | Wenchell et al. |
| 2016/0338694 A1 | 11/2016 | Kayan |
| 2016/0345967 A1 | 12/2016 | Sniffin et al. |
| 2017/0181789 A1* | 6/2017 | Ding .................. A61B 18/1445 |
| 2017/0231631 A1 | 8/2017 | Abuzaina et al. |
| 2017/0265859 A1* | 9/2017 | Sniffin ................ A61B 17/068 |
| 2017/0333092 A1* | 11/2017 | McGahan .......... A61B 17/7074 |
| 2018/0042591 A1 | 2/2018 | Russo et al. |
| 2018/0116670 A1 | 5/2018 | Fischvogt et al. |
| 2018/0242977 A1* | 8/2018 | Tan .................... A61B 17/1285 |

FOREIGN PATENT DOCUMENTS

| | | | |
|---|---|---|---|
| CN | 201438958 | 4/2010 | |
| CN | 102413863 | 4/2012 | |
| CN | 101933795 | 9/2012 | |
| DE | 10300787 A1 | 9/2004 | |
| DE | 10 2010 015009 A1 | 10/2011 | |
| EP | 0374088 A1 | 6/1990 | |
| EP | 0834280 A1 | 4/1998 | |
| EP | 1273272 A2 | 1/2003 | |
| EP | 1908409 A1 * | 4/2008 | ........... A61B 17/068 |
| EP | 1990013 A1 | 11/2008 | |
| EP | 2 055 241 A2 | 5/2009 | |
| EP | 1908409 B1 | 12/2010 | |
| EP | 2399538 A2 | 12/2011 | |
| EP | 2484294 A1 | 8/2012 | |
| JP | 09149906 | 6/1997 | |
| WO | 00/16701 A1 | 3/2000 | |
| WO | 2002/034140 A2 | 5/2002 | |
| WO | 2003/034925 A2 | 5/2003 | |
| WO | 2003/103507 A2 | 12/2003 | |
| WO | 2004/112841 A2 | 12/2004 | |
| WO | 2005004727 A1 | 1/2005 | |
| WO | WO-2008130826 | 10/2008 | |
| WO | 2009/039506 A1 | 3/2009 | |
| WO | WO-2010135325 | 11/2010 | |
| WO | 2012/064692 A2 | 5/2012 | |
| WO | 2013/046115 A1 | 4/2013 | |
| WO | WO-2015149292 A1 * | 10/2015 | ....... A61B 17/00234 |
| WO | WO-2016000245 A1 * | 1/2016 | ........... A61B 17/068 |
| WO | WO-2016000246 A1 * | 1/2016 | ........... A61B 17/068 |
| WO | WO-2016000255 A1 * | 1/2016 | ........... A61B 17/068 |
| WO | WO-2016011594 A1 * | 1/2016 | ........... A61B 17/068 |

OTHER PUBLICATIONS

Japanese Office Action corresponding to Patent Application JP 2014-132105 dated May 1, 2018.
Japanese Office Action corresponding to Patent Application JP 2014-047708 dated May 14, 2018.
Chinese Second Office Action corresponding to Patent Application CN 2014103559671 dated May 25, 2018.
Australian Examination Report No. 1 corresponding to Patent Application AU 2014302551 dated Jul. 16, 2018.
Japanese Office Action corresponding to Patent Application JP 2014-047708 dated Aug. 15, 2018.
Chinese Second Office Action corresponding to counterpart Chinese Appln. No. 201480077682.4 dated Mar. 21, 2018.
International Search Report for (PCT/CN2014/074583) date of completion is Dec. 4, 2014 (3 pages).
Extended European Search Report corresponding to counterpart application EP 10 01 2659.8, completed Dec. 21, 2010 and dated Jan. 3, 2011; 3 pages.
Extended European Search Report corresponding to counterpart application EP 10 01 26465, completed Feb. 11, 2011 and dated Feb. 22, 2011; 10 pages.
Extended European Search Report corresponding to counterpart application EP 11 25 0549.0, completed Sep. 9, 2013 and dated Sep. 17, 2013; 9 pages.
Extended European Search Report corresponding to counterpart application EP 14 15 9394.7, completed Apr. 16, 2014 and dated Apr. 29, 2014; 8 pages.
Extended European Search Report corresponding to counterpart application EP 14 15 89465, completed Jun. 20, 2014 and dated Jul. 8, 2014; (9 pp).
Extended European Search Report corresponding to counterpart application EP 14 17 8107.0, completed Nov. 24, 2014 and dated Dec. 3, 2014; (5 pp).
Extended European Search Report corresponding to counterpart application EP 14 17 4656.0, completed Jan. 16, 2015 and dated Jan. 26, 2015; (7 pp).
Extended European Search Report corresponding to counterpart application EP 14 18 49075, completed Jan. 12, 2015 and dated Jan. 27, 2015; (9 pp).
Extended European Search Report corresponding to counterpart Int'l Application No. EP 14 18 1900.3 dated Apr. 9, 2015.
Extended European Search Report corresponding to counterpart Int'l, Application No. EP 14 19 7885.8 dated Mar. 30, 2015.
Chinese First Office Action corresponding to Chinese Patent Appln. No. 201480037169.2 dated Jun. 29, 2017.
Chinese First Office Action corresponding to Chinese Patent Appln. No. 201410418879.1 dated Jun. 29, 2017.
European Office Action corresponding to European Patent Appln. No. 14 17 8107.0 dated Oct. 12, 2017.
Australian Examination Report No. 1 corresponding to Australian Patent Appln. No. 2014200870 dated Oct. 26, 2017.
Chinese Second Office Action corresponding to Chinese Patent Appln. No. 201410090675 dated Nov. 6, 2017.
Japanese Office Action corresponding to Japanese Patent Appln. No. 2014-048652 dated Nov. 14, 2017.
Japanese Office Action corresponding to Japanese Patent Appln. No. 2014-047708 dated Nov. 14, 2017.
Chinese Second Office Action corresponding to Chinese Patent Appln. No. 2014103063407 dated Feb. 1, 2018.
Australian Examination Report No. 1 corresponding to Australian Patent Appln. No. 2014202970 dated Mar. 9, 2018.
Japanese Office Action corresponding to Japanese Patent Appln. No. 2014-048652 dated Mar. 15, 2018.
Chinese Second Office Action corresponding to Chinese Patent Appln. No. 2014800776824 dated Mar. 21, 2018.
Australian Examination Report No. 1 corresponding to Australian Patent Appln. No. 2014202972 dated Mar. 27, 2018.
Extended European Search Report corresponding to Int'l, Application No. EP 14 15 1663.3 dated Jun. 7, 2016.

* cited by examiner

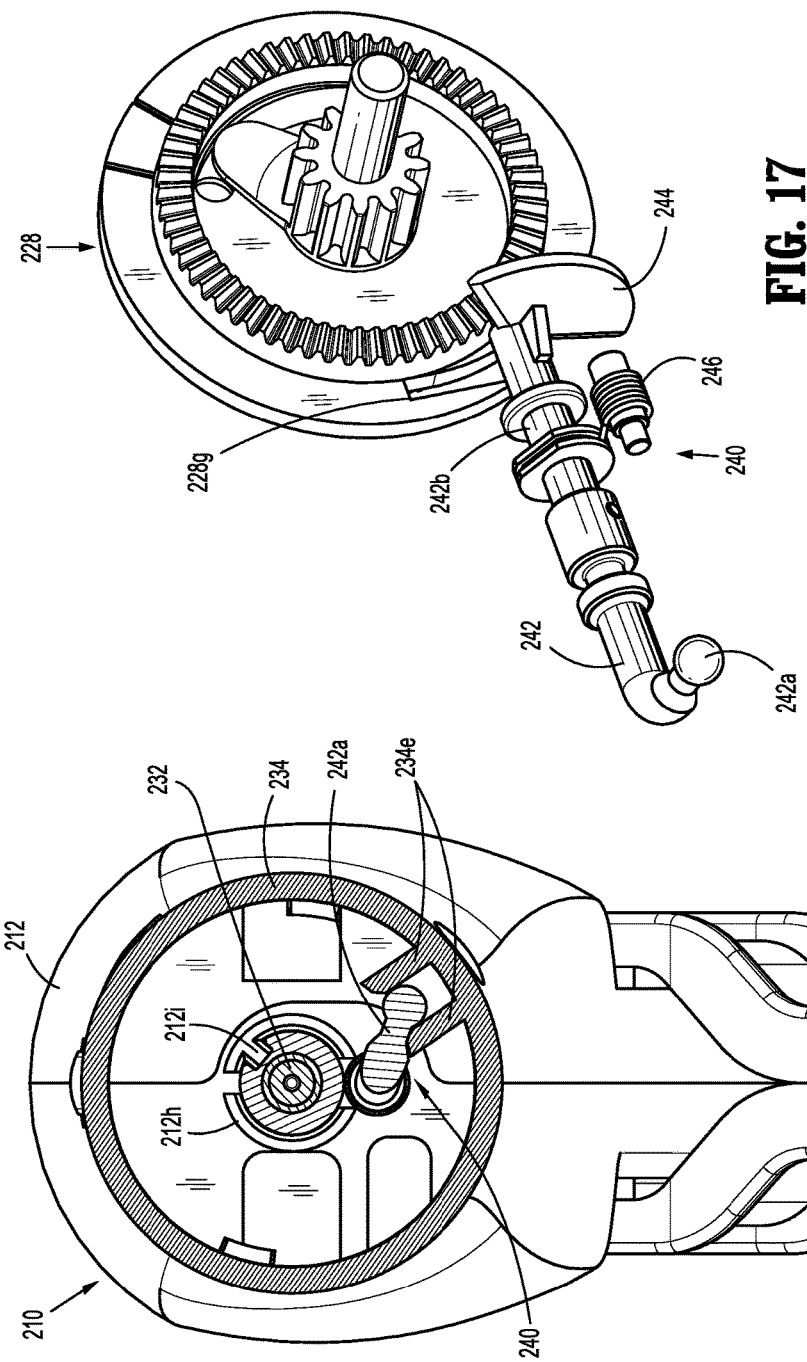

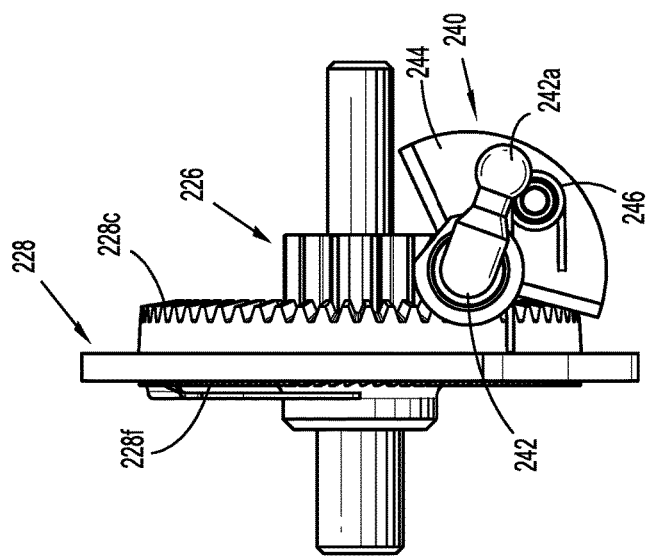
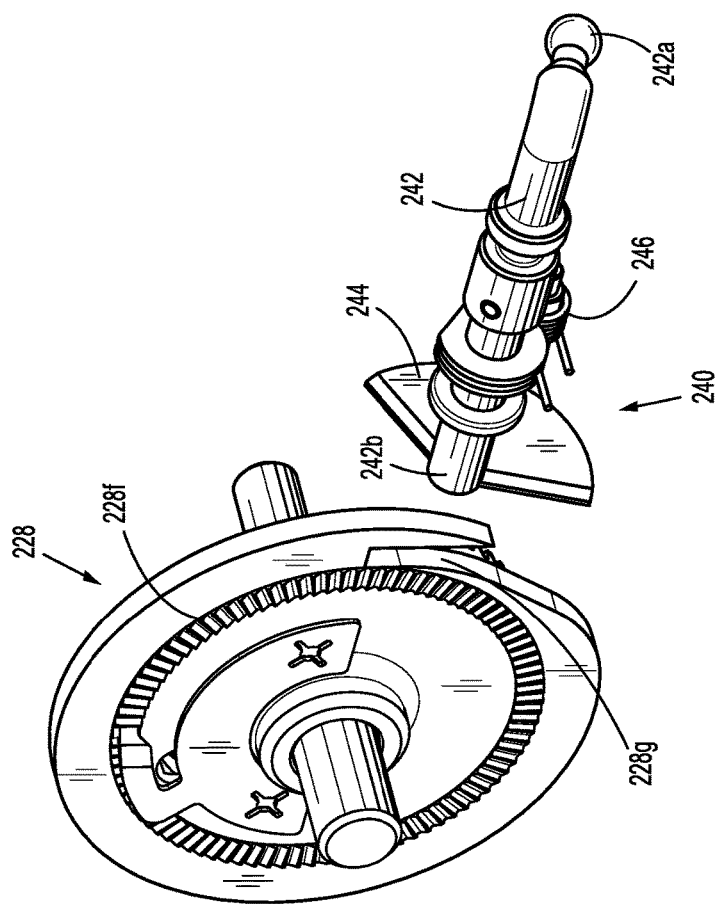
FIG. 19
FIG. 18

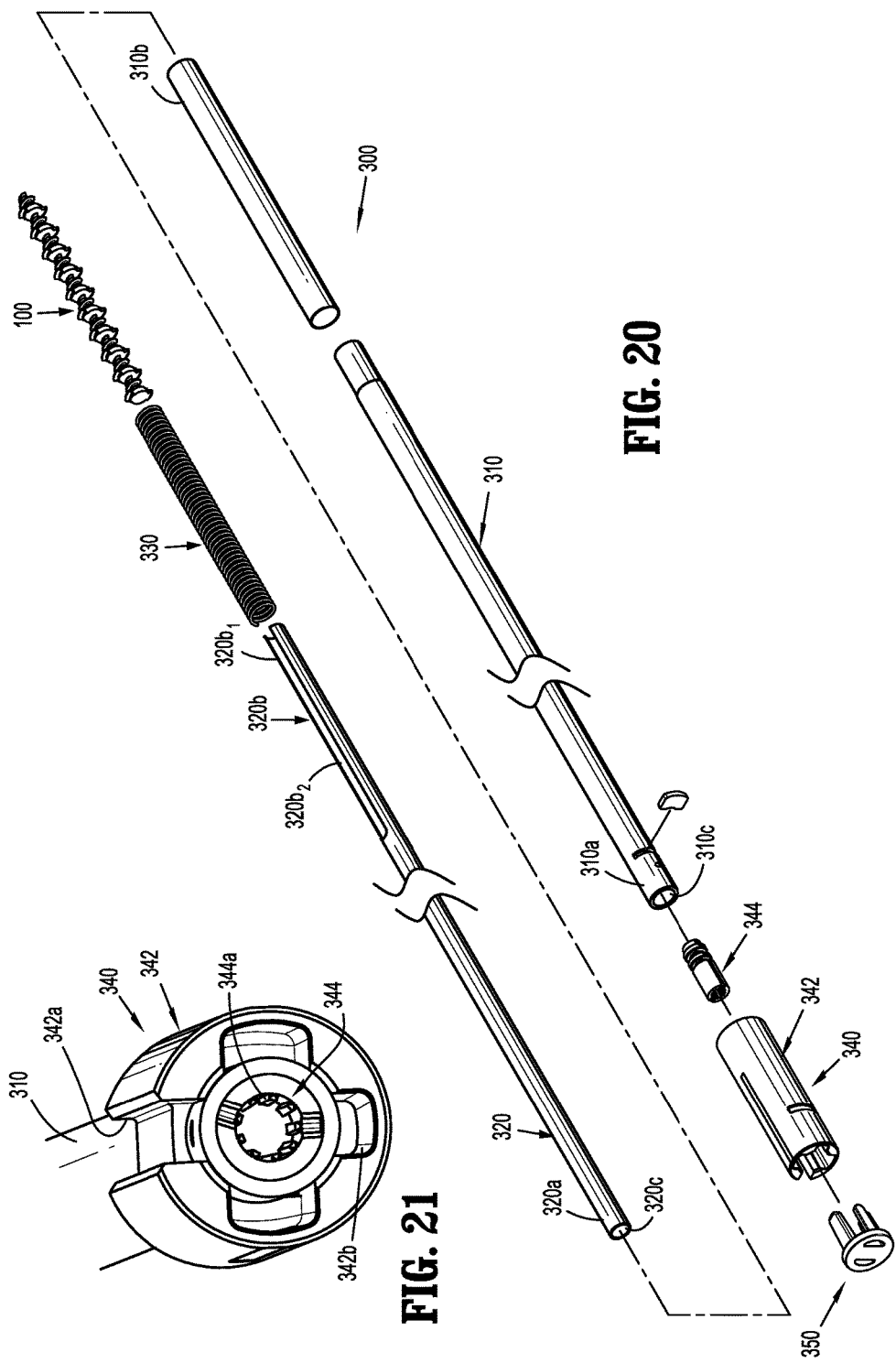

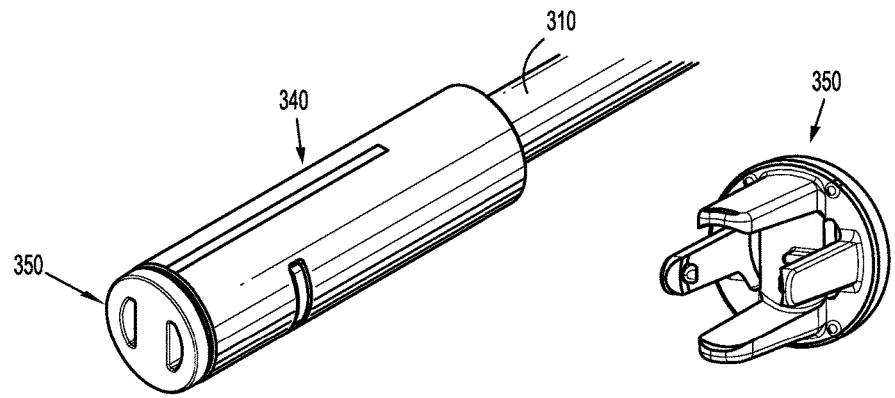
FIG. 22   FIG. 23
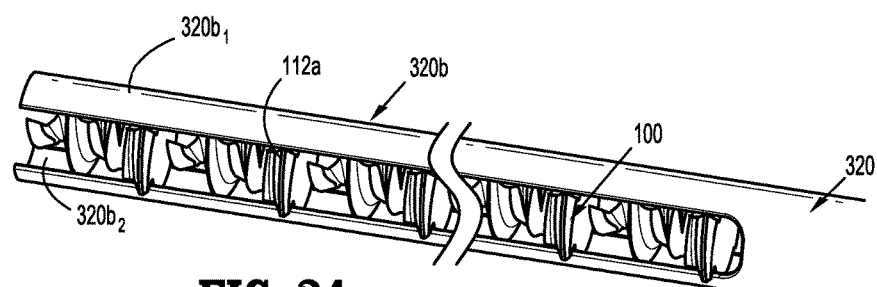
FIG. 24
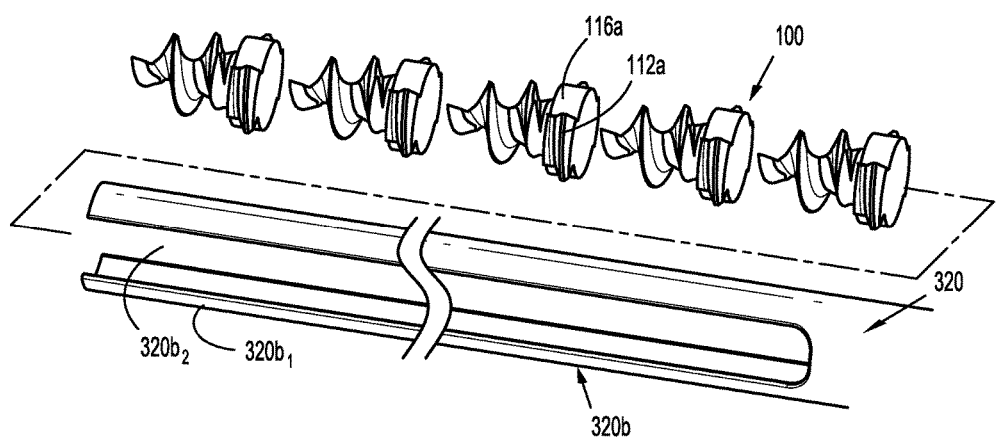
FIG. 25

SURGICAL FASTENER APPLYING APPARATUS, KITS AND METHODS FOR ENDOSCOPIC PROCEDURES

CROSS-REFERENCE TO RELATED APPLICATIONS

This application is a U.S. National Stage Application filed under 35 U.S.C. § 371(a), which claims priority and benefit of International Patent Application Serial No. PCT/CN2014/074583, filed Apr. 2, 2014, the entire disclosure of which is incorporated by reference herein.

BACKGROUND

1. Technical Field

The present disclosure relates to a surgical apparatus, device and/or system for performing endoscopic surgical procedures and methods of use thereof. More specifically, the present disclosure relates to a surgical fastener applying apparatus, device and/or system for performing endoscopic surgical procedures, which is loadable with disposable endoscopic loading units containing absorbable or permanent surgical fasteners, to kits, and methods of use thereof.

2. Background of Related Art

Various surgical procedures require instruments capable of applying fasteners to tissue to form tissue connections or to secure objects to tissue. For example, during hernia repair it is often desirable to fasten a mesh to body tissue. In certain hernias, such as direct or indirect inguinal hernias, a part of the intestine protrudes through a defect in the abdominal wall to form a hernial sac. The defect may be repaired using an open surgery procedure in which a relatively large incision is made and the hernia is closed outside the abdominal wall by suturing. The mesh is attached with sutures over the opening in the abdominal wall to provide reinforcement.

Minimally invasive, e.g., endoscopic or laparoscopic, surgical procedures are currently available to repair a hernia. In laparoscopic procedures, surgery is performed in the abdomen through a small incision while in endoscopic procedures, surgery is performed through narrow endoscopic tubes or cannulas inserted through small incisions in the body. Laparoscopic and endoscopic procedures generally utilize long and narrow instruments capable of reaching remote regions within the body and configured to seal with the incision or tube they are inserted through. Additionally, the instruments must be capable of being actuated remotely, that is, from outside the body.

Currently, minimally invasive surgical techniques for hernia repair utilize surgical fasteners, e.g., surgical tacks, staples, and clips, to secure the mesh to the tissue to provide reinforcement and structure for encouraging tissue ingrowth. Surgical fasteners are often applied through an elongate instrument for delivery to the mesh, and are manipulated from outside a body cavity.

In some procedures permanent fasteners may be required, while in other procedures bioabsorbable fasteners may be required, or both. The laparoscopic or endoscopic instruments are typically loaded with either permanent fasteners or bioabsorbable fasteners. Additionally, following a surgical procedure, these laparoscopic or endoscopic instruments are typically disposed.

Accordingly, a need exists for endoscopic or laparoscopic surgical devices which can be loaded with either permanent fasteners or bioabsorbable fasteners as needed or desired, and which may be at least partially sterilized for re-use following a surgical procedure.

SUMMARY

The present disclosure relates to surgical devices for performing endoscopic surgical procedures which are loadable with disposable endoscopic loading units loaded with absorbable or permanent surgical fasteners, kits, and methods of use thereof.

According to an aspect of the present disclosure, an endoscopic surgical device is provided and includes a handle assembly including a handle housing and a trigger operatively connected to the handle housing, and a drive mechanism actuatable by the trigger; and an endoscopic assembly selectively connectable to the handle assembly. The endoscopic assembly includes an outer tube defining a lumen therethrough and having a helical thread disposed within the lumen thereof, the outer tube defining a proximal end and a distal end; an inner tube rotatably supported in the outer tube, the inner tube defining a lumen therethrough and having a proximal end and a splined distal end, wherein the splined distal end of the inner tube is defined by a pair of opposed longitudinally extending tines and a pair of opposed longitudinally extending channels; a plurality of surgical anchors loaded in the lumen of the inner tube of the endoscopic assembly, wherein each anchor includes a threaded body portion, and a head portion defining a pair of opposed radially outer threads and a pair of opposed radial recesses, wherein the pair of radial recesses of each head portion receives respective tines of the inner tube and wherein the pair of opposed radially outer threads of each head portion projects from the pair of opposed longitudinally extending channels of the inner tube and engage the inner helical thread of the outer tube; and a connector.

The connector includes an outer connector member non-rotatably connected to the proximal end of the outer tube and being non-rotatably connectable to the handle assembly; and an inner connector member non-rotatably connected to the proximal end of the inner tube and being non-rotatably connectable to the drive mechanism, wherein the outer connector member and the inner connector member are rotatable with respect to one another.

The handle housing may include a tooth projecting from a surface thereof, and wherein the outer connector member may include a channel formed therein. The channel of the outer connector member may receive the tooth of the handle housing when the endoscopic assembly is connected to the handle assembly. The tooth may inhibit rotation of the outer connector member when the trigger is actuated to rotate the inner connector member of the endoscopic assembly.

The handle assembly may include a ferrule removably and rotatably connected to the handle housing. The ferrule may define an aperture therein that is in operative alignment with the drive mechanism of the handle assembly. The ferrule may include a tooth projecting radially into the aperture of the ferrule.

The ferrule may have a first position wherein the tooth of the ferrule is radially aligned with the tooth of the handle housing; and a second position wherein the tooth of the ferrule is radially out of alignment with the tooth of the handle housing.

In use, when the ferrule is in the first position the endoscopic assembly may be connectable to and disconnectable from the handle assembly.

The channel of the outer connector member may be formed in an outer radial surface thereof and may extend axially along an entire length thereof. During connection of the endoscopic assembly to the handle assembly and disconnection of the endoscopic assembly from the handle assembly, the tooth of the ferrule may pass along the channel of the outer connector member.

The outer channel of the outer connector member may define a length. In use, when the endoscopic assembly is connected to the handle assembly, the tooth of the ferrule may be disposed distally of the channel of the outer connector member, and wherein the ferrule may be rotatable to the second position such that the tooth of the ferrule may inhibit disconnection of the endoscopic assembly and handle assembly from one another.

The ferrule may be rotatable to a third position wherein the ferrule may be disconnectable from the handle housing.

The handle assembly may include a safety lock assembly supported on the handle housing. The safety lock assembly may include a proximal end disposed within the handle housing and being in operative association with the drive mechanism, and a distal end projecting from the handle housing and being in operative association with the ferrule.

In use, when the ferrule is in the first position, the safety lock assembly may be in a first position such that the proximal end of the safety lock assembly may engage the drive mechanism to block operation of the drive mechanism. Also in use, when the ferrule is in the second position, the safety lock assembly may be in a second position such that the proximal end of the safety lock assembly is disengaged from the drive mechanism to permit operation of the drive mechanism.

The ferrule may actuate the safety lock assembly between the first and second positions thereof as the ferrule is moved between respective first and second positions thereof.

The safety lock assembly may include a lock plate supported on and extending radially from the proximal end thereof. The lock plate may have a generally pie-shaped profile. The drive mechanism may include a gear defining a slot therein. In use, the lock plate of the safety lock assembly may be disposed within the slot of the gear of the drive mechanism when the ferrule is in the first position.

The drive mechanism may include a plurality of gears, wherein at least one gear is actuated by the trigger, and wherein at least one gear actuates a drive shaft extending from the handle housing. The drive shaft may be keyed for selective connection to the inner connector member supported at the proximal end of the inner tube.

According to another aspect of the present disclosure, an endoscopic surgical device is provided and includes a handle assembly including a handle housing and a trigger operatively connected to the handle housing, and a drive mechanism actuatable by the trigger; and an endoscopic assembly selectively connectable to the handle assembly.

The endoscopic assembly includes an outer tube defining a lumen therethrough; an inner tube rotatably supported in the outer tube and defining a lumen therethrough; a plurality of surgical anchors loaded in the lumen of the inner tube of the endoscopic assembly, wherein each anchor includes a threaded body portion and a head portion acted upon by the inner tube to axially advanced the fire the surgical anchors from the endoscopic assembly; and a connector.

The connector includes an outer connector member non-rotatably connected to a proximal end of the outer tube and being non-rotatably connectable to the handle assembly; and an inner connector member non-rotatably connected to a proximal end of the inner tube and being non-rotatably connectable to the drive mechanism, wherein the outer connector member and the inner connector member are rotatable with respect to one another.

The handle housing may include a tooth projecting from a surface thereof, and the outer connector member may include a channel formed therein. The channel of the outer connector member may receive the tooth of the handle housing when the endoscopic assembly is connected to the handle assembly. In use, the tooth may inhibit rotation of the outer connector member when the trigger is actuated to rotate the inner connector member of the endoscopic assembly.

The handle assembly may include a ferrule removably and rotatably connected to the handle housing. The ferrule may define an aperture therein that is in operative alignment with the drive mechanism of the handle assembly. The ferrule may include a tooth projecting radially into the aperture of the ferrule. The ferrule may have a first position wherein the tooth of the ferrule is radially aligned with the tooth of the handle housing; and a second position wherein the tooth of the ferrule is radially out of alignment with the tooth of the handle housing.

In use, when the ferrule is in the first position the endoscopic assembly may be connectable to and disconnectable from the handle assembly.

The channel of the outer connector member may be formed in an outer radial surface thereof and may extend axially along an entire length thereof. In use, during connection of the endoscopic assembly to the handle assembly and disconnection of the endoscopic assembly from the handle assembly, the tooth of the ferrule may pass along the channel of the outer connector member.

The outer channel of the outer connector member may define a length. In use, when the endoscopic assembly is connected to the handle assembly, the tooth of the ferrule may be disposed distally of the channel of the outer connector member, and wherein the ferrule may be rotatable to the second position such that the tooth of the ferrule inhibits disconnection of the endoscopic assembly and handle assembly from one another.

The ferrule may be rotatable to a third position wherein the ferrule is disconnectable from the handle housing.

The handle assembly may include a safety lock assembly supported on the handle housing. The safety lock assembly may include a proximal end disposed within the handle housing and being in operative association with the drive mechanism, and a distal end projecting from the handle housing and being in operative association with the ferrule.

In use, when the ferrule is in the first position, the safety lock assembly may be in a first position such that the proximal end of the safety lock assembly engages the drive mechanism to block operation of the drive mechanism. Also in use, when the ferrule is in the second position, the safety lock assembly may be in a second position such that the proximal end of the safety lock assembly is disengaged from the drive mechanism to permit operation of the drive mechanism.

The ferrule may actuate the safety lock assembly between the first and second positions thereof as the ferrule is moved between respective first and second positions thereof.

The safety lock assembly may include a lock plate supported on and extending radially from the proximal end thereof. The lock plate may have a generally pie-shaped profile. The drive mechanism may include a gear defining a slot therein. In use, wherein the lock plate of the safety lock assembly may be disposed within the slot of the gear of the drive mechanism when the ferrule is in the first position.

The drive mechanism may include a plurality of gears, wherein at least one gear is actuated by the trigger, and wherein at least one gear actuates a drive shaft extending from the handle housing. The drive shaft may be keyed for selective connection to the inner connector member supported at the proximal end of the inner tube.

The outer tube may include a helical thread disposed within the lumen thereof. The inner tube may define a splined distal end, wherein the splined distal end of the inner tube is defined by a pair of opposed longitudinally extending tines and a pair of opposed longitudinally extending channels. The head portion of each of the plurality of surgical anchors may define a pair of opposed radially outer threads and a pair of opposed radial recesses, wherein the pair of radial recesses of each head portion receives respective tines of the inner tube and wherein the pair of opposed radially outer threads of each head portion projects from the pair of opposed longitudinally extending channels of the inner tube and engage the inner helical thread of the outer tube.

According to yet another aspect of the present disclosure, an endoscopic surgical device is provided and includes a handle assembly including a handle housing and a trigger operatively connected to the handle housing, wherein the handle housing includes a tooth projecting from a surface thereof; a drive mechanism actuatable by the trigger; and a ferrule removably and rotatably connected to the handle housing, the ferrule defining an aperture therein that is in operative alignment with the drive mechanism of the handle assembly, the ferrule including a tooth projecting radially into the aperture of the ferrule.

The ferrule has a first position wherein the tooth of the ferrule is radially aligned with the tooth of the handle housing; and a second position wherein the tooth of the ferrule is radially out of alignment with the tooth of the handle housing.

The endoscopic surgical device further includes an endoscopic assembly extending from the handle assembly. The endoscopic assembly includes an outer tube defining a lumen therethrough and a helical inner coil; an inner tube rotatably supported in the outer tube and defining a lumen therethrough; a plurality of surgical anchors loaded in the lumen of the inner tube of the endoscopic assembly, wherein each anchor includes a threaded body portion and a head portion extending radially beyond the inner tube and engaging the helical inner coil; and a connector.

The connector has an outer connector member non-rotatably connected to a proximal end of the outer tube, being insertable through the aperture of the ferrule and being non-rotatably connectable to the handle assembly, wherein the outer connector member defines a channel formed therein that is configured to receive the tooth of the ferrule when the endoscopic assembly is connected to the handle assembly; and an inner connector member non-rotatably connected to a proximal end of the inner tube and being non-rotatably connectable to the drive mechanism, wherein the outer connector member and the inner connector member are rotatable with respect to one another.

In use, the channel of the outer connector member may receive the tooth of the handle housing when the endoscopic assembly is connected to the handle assembly. Further in use, the tooth may inhibit rotation of the outer connector member when the trigger is actuated to rotate the inner connector member of the endoscopic assembly.

In use, when the ferrule is in the first position the endoscopic assembly may be connectable to and disconnectable from the handle assembly.

The channel of the outer connector member may be formed in an outer radial surface thereof and may extend axially along an entire length thereof. In use, during connection of the endoscopic assembly to the handle assembly and disconnection of the endoscopic assembly from the handle assembly, the tooth of the ferrule may pass along the channel of the outer connector member.

The outer channel of the outer connector member may define a length. In use, when the endoscopic assembly is connected to the handle assembly, the tooth of the ferrule may be disposed distally of the channel of the outer connector member, and wherein the ferrule is rotatable to the second position such that the tooth of the ferrule may inhibit disconnection of the endoscopic assembly and handle assembly from one another.

The ferrule may be rotatable to a third position wherein the ferrule is disconnectable from the handle housing.

The handle assembly may include a safety lock assembly supported on the handle housing. The safety lock assembly may include a proximal end disposed within the handle housing and being in operative association with the drive mechanism, and a distal end projecting from the handle housing and being in operative association with the ferrule.

In use, when the ferrule is in the first position, the safety lock assembly may be in a first position such that the proximal end of the safety lock assembly engages the drive mechanism to block operation of the drive mechanism. Also in use, when the ferrule is in the second position, the safety lock assembly may be in a second position such that the proximal end of the safety lock assembly is disengaged from the drive mechanism to permit operation of the drive mechanism.

The ferrule may actuate the safety lock assembly between the first and second positions thereof as the ferrule is moved between respective first and second positions thereof.

The safety lock assembly may include a lock plate supported on and extending radially from the proximal end thereof. The lock plate may have a generally pie-shaped profile. The drive mechanism may include a gear defining a slot therein. In use, the lock plate of the safety lock assembly may be disposed within the slot of the gear of the drive mechanism when the ferrule is in the first position.

The drive mechanism may include a plurality of gears, wherein at least one gear may be actuated by the trigger, and wherein at least one gear may actuate a drive shaft extending from the handle housing. The drive shaft may be keyed for selective connection to the inner connector member supported at the proximal end of the inner tube.

The outer tube may include a helical thread disposed within the lumen thereof. The inner tube may define a splined distal end, wherein the splined distal end of the inner tube is defined by a pair of opposed longitudinally extending tines and a pair of opposed longitudinally extending channels. The head portion of each of the plurality of surgical anchors may define a pair of opposed radially outer threads and a pair of opposed radial recesses, wherein the pair of radial recesses of each head portion receives respective tines of the inner tube and wherein the pair of opposed radially outer threads of each head portion projects from the pair of opposed longitudinally extending channels of the inner tube and engage the inner helical thread of the outer tube.

According to yet another aspect of the present disclosure, an endoscopic surgical device is provided and includes a handle assembly including a handle housing and a trigger operatively connected to the handle housing, wherein the handle housing includes a tooth projecting from a surface thereof; a drive mechanism actuatable by the trigger; and a ferrule removably and rotatably connected to the handle housing, the ferrule defining an aperture therein that is in operative alignment with the drive mechanism of the handle assembly, the ferrule including a tooth projecting radially into the aperture of the ferrule.

The ferrule has a first position wherein the tooth of the ferrule is radially aligned with the tooth of the handle housing; and a second position wherein the tooth of the ferrule is radially out of alignment with the tooth of the handle housing.

The handle assembly further includes a safety lock assembly supported on the handle housing, the safety lock assembly includes a proximal end disposed within the handle housing and being in operative association with the drive mechanism, and a distal end projecting from the handle housing and being in operative association with the ferrule.

In use, when the ferrule is in the first position, the safety lock assembly is in a first position such that the proximal end of the safety lock assembly engages the drive mechanism to block operation of the drive mechanism; and when the ferrule is in the second position, the safety lock assembly is in a second position such that the proximal end of the safety lock assembly is disengaged from the drive mechanism to permit operation of the drive mechanism.

The ferrule may actuate the safety lock assembly between the first and second positions thereof as the ferrule is moved between respective first and second positions thereof.

The safety lock assembly may include a lock plate supported on and extending radially from the proximal end thereof. The lock plate may have a generally pie-shaped profile. The drive mechanism may include a gear defining a slot therein. In use, the lock plate of the safety lock assembly may be disposed within the slot of the gear of the drive mechanism when the ferrule is in the first position.

The endoscopic surgical device may further include an endoscopic assembly extending from the handle assembly. The endoscopic assembly may include an outer tube defining a lumen therethrough and a helical inner coil; an inner tube rotatably supported in the outer tube and defining a lumen therethrough; a plurality of surgical anchors loaded in the lumen of the inner tube of the endoscopic assembly, wherein each anchor includes a threaded body portion and a head portion extending radially beyond the inner tube and engaging the helical inner coil; and a connector.

The connector may have an outer connector member non-rotatably connected to a proximal end of the outer tube and which is insertable through the aperture of the ferrule and being non-rotatably connectable to the handle assembly, wherein the outer connector member defines a channel formed therein that is configured to receive the tooth of the ferrule and the tooth of the handle housing when the endoscopic assembly is connected to the handle assembly. The connector may also have an inner connector member non-rotatably connected to a proximal end of the inner tube and being non-rotatably connectable to the drive mechanism. The outer connector member and the inner connector member may be rotatable with respect to one another.

The drive mechanism may include a plurality of gears, wherein at least one gear is actuated by the trigger, and wherein at least one gear actuates a drive shaft extending from the handle housing, wherein the drive shaft is keyed for selective connection to the inner connector member supported at the proximal end of the inner tube.

The outer tube may include a helical thread disposed within the lumen thereof; the inner tube may define a splined distal end, wherein the splined distal end of the inner tube is defined by a pair of opposed longitudinally extending tines and a pair of opposed longitudinally extending channels; and the head portion of each of the plurality of surgical anchors may define a pair of opposed radially outer threads and a pair of opposed radial recesses. The pair of radial recesses of each head portion may receive respective tines of the inner tube and the pair of opposed radially outer threads of each head portion may project from the pair of opposed longitudinally extending channels of the inner tube and engage the inner helical thread of the outer tube.

Further details and aspects of exemplary embodiments of the present disclosure are described in more detail below with reference to the appended figures.

BRIEF DESCRIPTION OF THE DRAWINGS

Embodiments of the present disclosure are described herein with reference to the accompanying drawings, wherein:

FIG. 16 is a cross-sectional view as taken through section line 16-16 of FIG. 6;

FIG. 17 is a front, perspective view of a lock out assembly and a first bevel gear of a gear train of the present disclosure;

FIG. 18 is a rear, perspective view of the lock out assembly and the first bevel gear of the gear train of the present disclosure;

FIG. 19 is a front, plan view of the lock out assembly and the first bevel gear of the gear train of the present disclosure;

FIG. 20 is a perspective view, with parts separated, of the endoscopic assembly of the surgical device of the present disclosure;

FIG. 21 is a rear, perspective view of the endoscopic assembly of the present disclosure;

FIG. 22 is a rear, perspective view of the endoscopic assembly of the present disclosure, illustrating a shipping plug connected thereto;

FIG. 23 is a perspective view of the shipping plug of the present disclosure;

FIG. 24 is a perspective view of a distal end portion of the endoscopic assembly with an outer tube and a coil removed therefrom, shown with surgical anchors loaded therein;

FIG. 25 is a perspective view of the distal end portion of the endoscopic assembly with the outer tube and the coil removed therefrom, shown with surgical anchors separated therefrom;

DETAILED DESCRIPTION OF EMBODIMENTS

Figure 1:
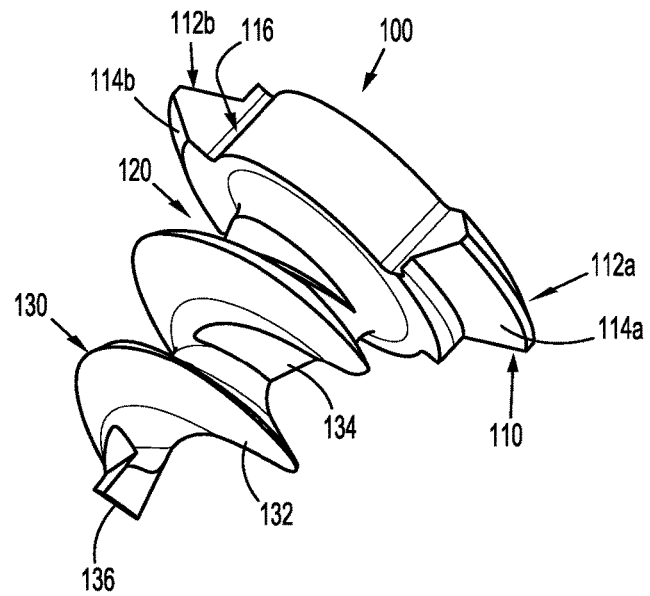
FIG. 1 is a perspective view of a surgical anchor for use in an endoscopic surgical device in accordance with the present disclosure.
Figure 2:
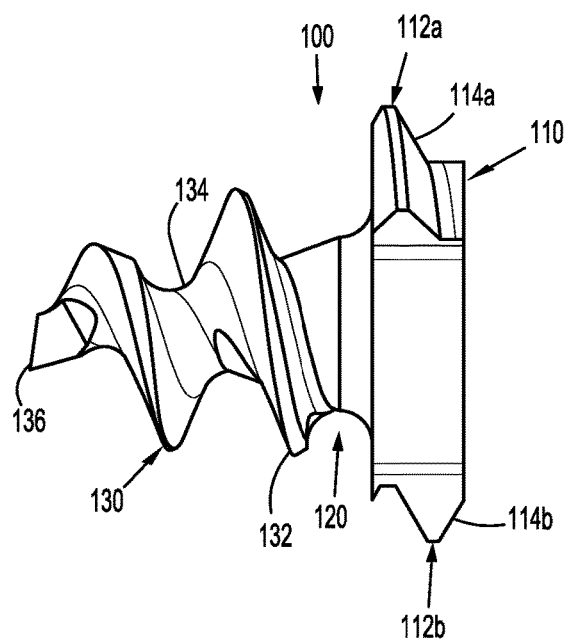
FIG. 2 is a side, elevational view of the surgical anchor of FIG. 1.
Figure 3:
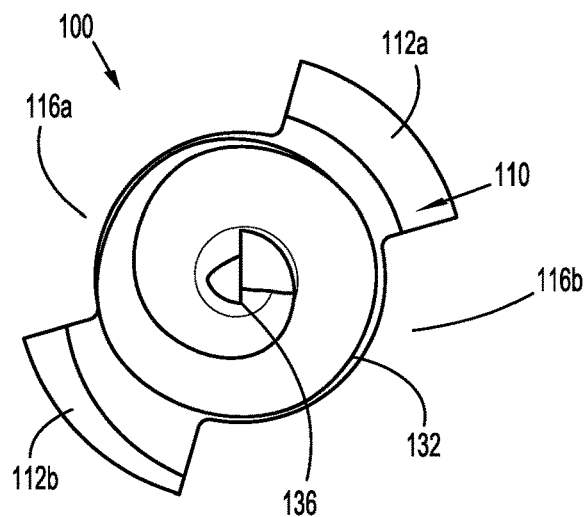
FIG. 3 is a distal, end view of the surgical anchor of FIGS. 1 and 2.

Embodiments of the presently disclosed endoscopic surgical device is described in detail with reference to the drawings, in which like reference numerals designate identical or corresponding elements in each of the several views. As used herein the term "distal" refers to that portion of the endoscopic surgical device, that is farther from the user, while the term "proximal" refers to that portion of the endoscopic surgical device that is closer to the user.

Referring initially to FIGS. 1-4, a surgical anchor for use with the surgical tack applier of the present disclosure is illustrated and generally designated as anchor 100. As illustrated in FIGS. 1-4, anchor 100 includes a head section 110, a mesh retention section 120, and a threaded tissue-snaring section 130. Head section 110 includes a pair of opposing threaded sections 112a, 112b having respective radially, outer, helical head threads 114a, 114b, and a pair of opposing open or slotted sections 116a, 116b. A distal surface of head section 110 is formed onto or integral with a proximal end of mesh retention section 120.

Mesh retention section 120 of anchor 100 extends from and between a distal end or surface of head section 110 and a proximal end of tissue-snaring section 130. Mesh retention section 120 functions to lock, anchor or otherwise retain a surgical mesh (not shown) on to anchor 100 when anchor 100 is screwed into the mesh to a depth past a proximal-most segment 138 of tissue-snaring thread 132 of tissue-snaring section 130. This is achieved because there is no thread located in mesh retention section 120 that would allow anchor 100 to be unscrewed or backed out from the mesh.

Mesh retention section 120 has a cylindrical or conical transverse cross-sectional profile. Mesh retention section 120 includes a transverse radial dimension, relative to a central longitudinal axis of anchor 100, that is smaller than a transverse radial dimension of head section 110, and smaller than a transverse radial dimension of proximal-most segment 138 of tissue-snaring thread 138.

Threaded tissue-snaring section 130 of anchor 100 includes helical threads 132 formed onto a tapered truncated body section 134. A distal point or tip 136 defines the terminus of the distal most tissue-snaring thread 132.

Figure 4:
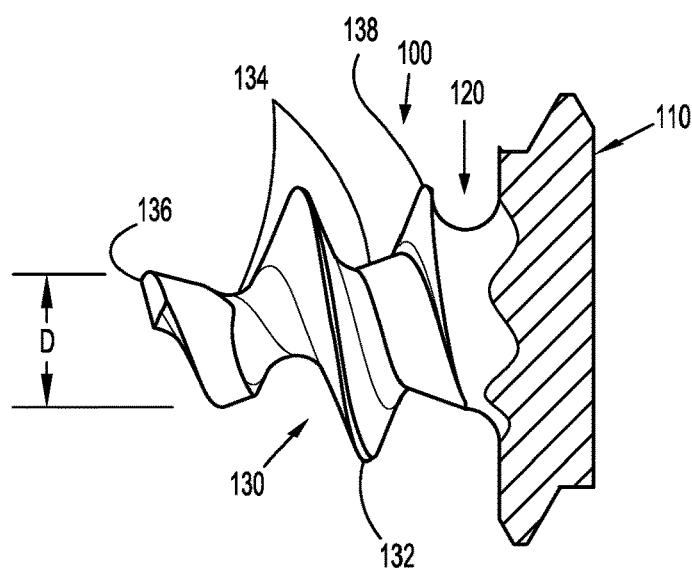
FIG. 4 is a side, elevational view, partially broken away, of the surgical anchor of FIGS. 1-3.
Figure 5:
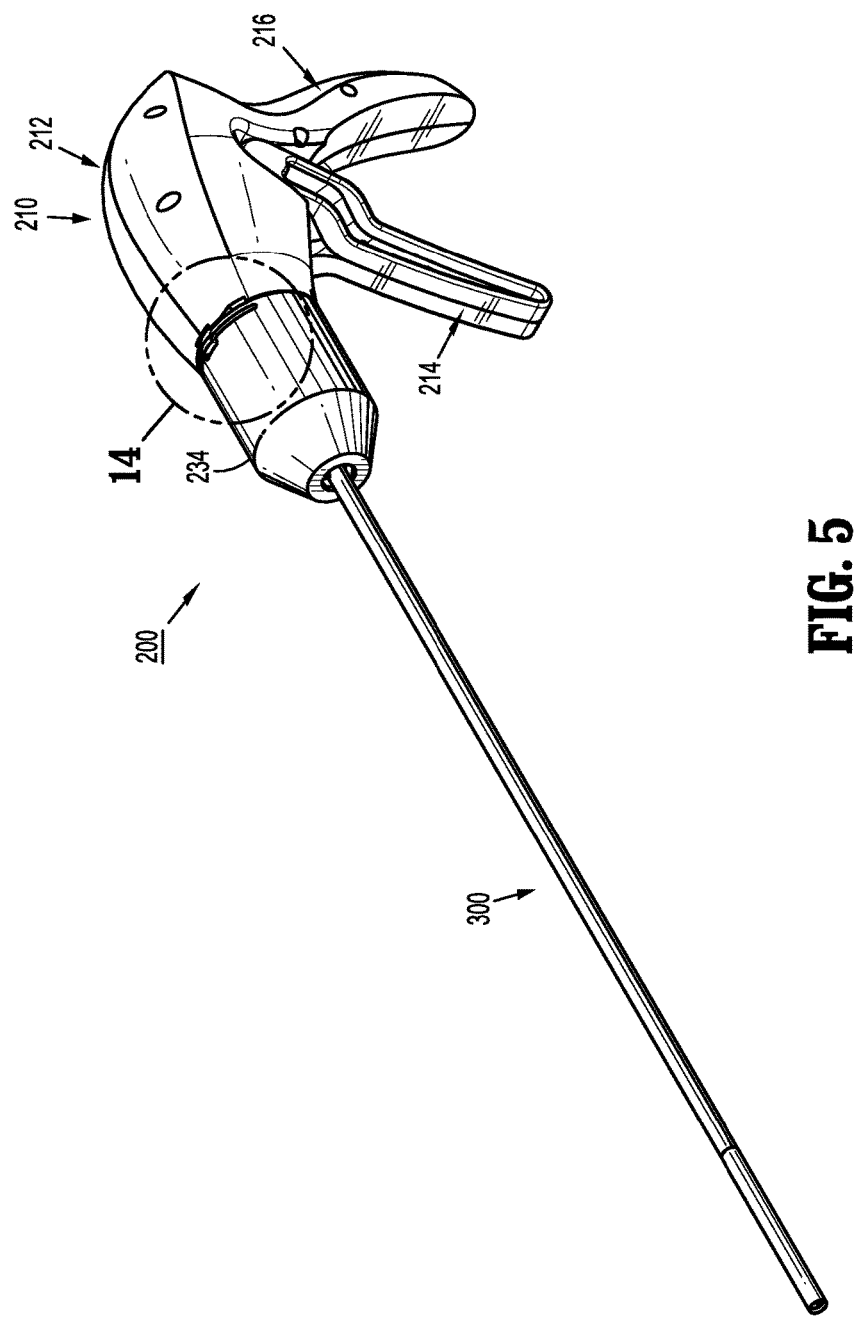
FIG. 5 is a perspective view of an endoscopic surgical device according to an aspect of the present disclosure.
Figure 6:
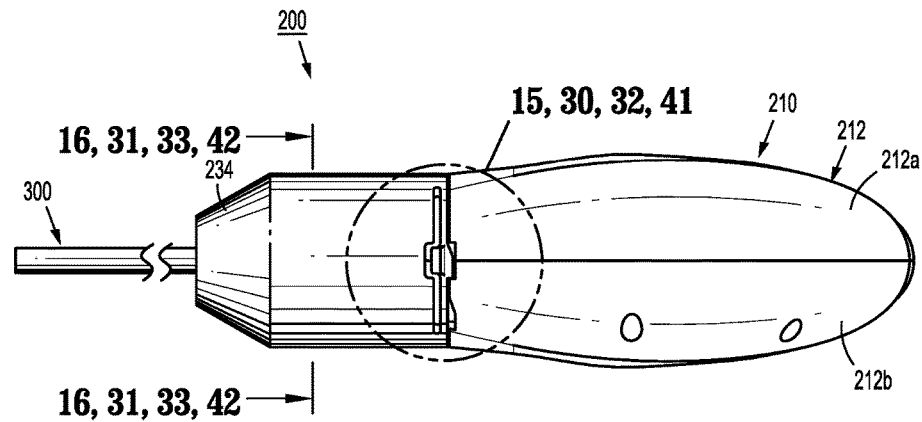
FIG. 6 is a top, plan view of the surgical device of FIG. 5.
Figure 7:
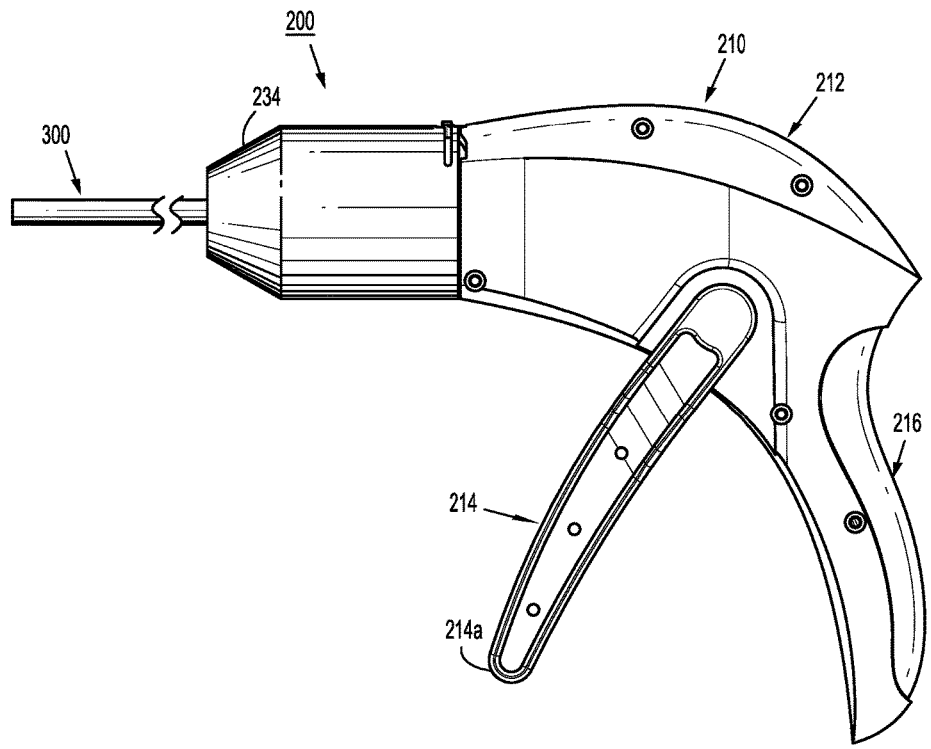
FIG. 7 is a side, elevational view of the surgical device of FIGS. 5 and 6.
Figure 8:
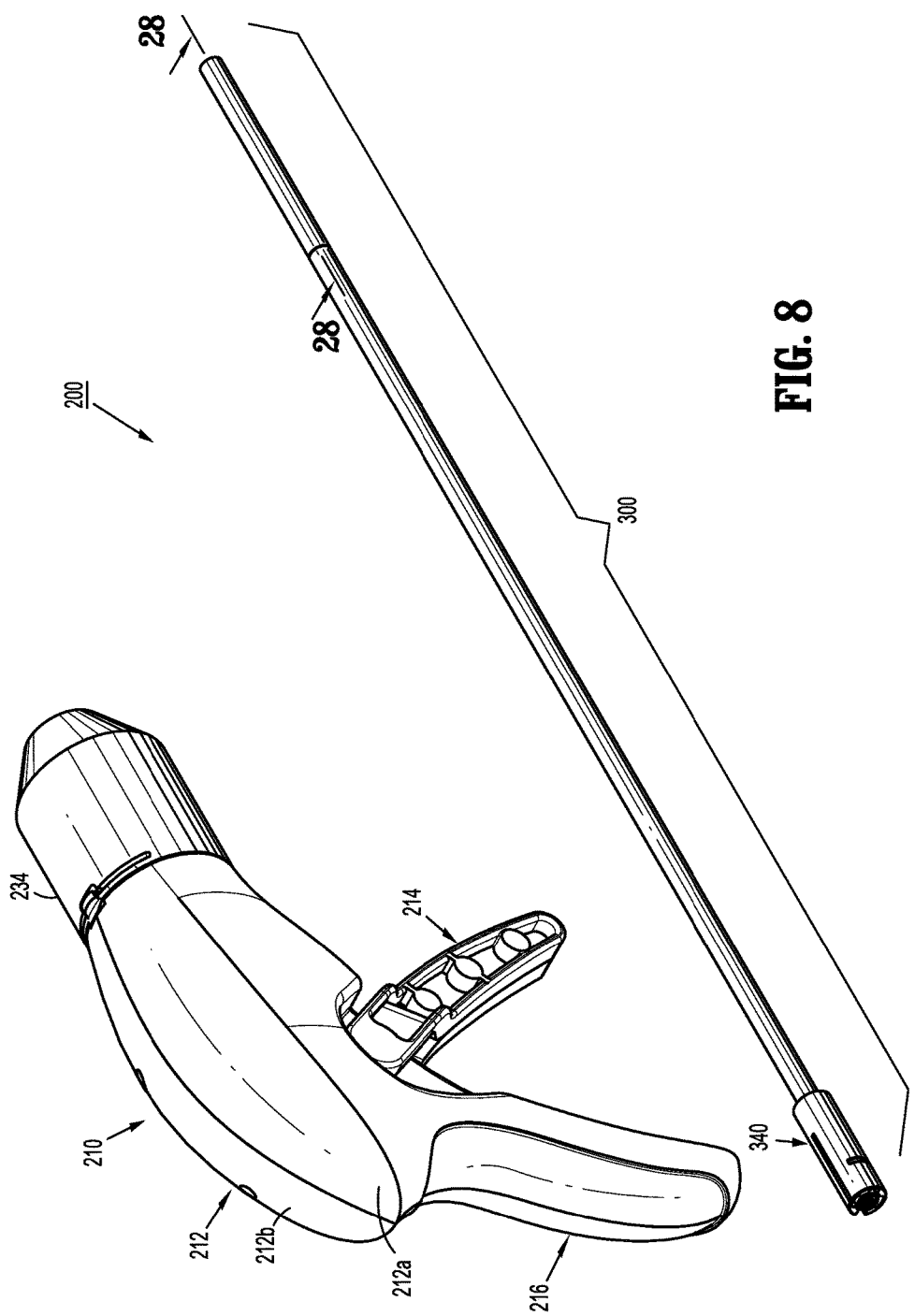
FIG. 8 is a rear, perspective view of the surgical device of FIGS. 5-7, illustrating a handle assembly and an endoscopic assembly thereof separated from one another.

As shown in FIG. 4, body section 134 of tissue-snaring section 130 is tapered, i.e., becoming smaller toward the distal end of threaded tissue-snaring section 130, and terminates or truncates to a distal truncation point "TP", prior to reaching an apex or tip of anchor 100. Body section 134 includes a concave taper such that, for a given length, a minimum diameter body section 134 is defined upon truncation thereof which is approximately less than 0.01 inches.

Anchor 100 includes a transverse dimension "D", of a distal-most thread in the threaded tissue-snaring section 130 which is as large as design constraints will allow or approximately greater than 0.040 inches. In accordance with the present disclosure, a small truncated body diameter and a large value of "D" minimizes tissue indentation. The tissue-snaring threads 132 terminate at distal tip 136, which is distal of the truncation point "TP" of body section 134.

By providing a distal tip 136 extending distally of truncation point "TP" of tissue-snaring section 130, a penetration of the mesh, by anchor 100, is eased; and an indentation of the mesh into relatively soft tissue, by anchor 100, is minimized, as compared to an anchor having a non-truncated body with tapered threads.

For a given force applied to a surgical mesh by the surgeon, exerting a distal force on a tack applier, the larger the dimension "D" of anchor 100, the less the distal force that needs to be exerted in order to cause indentation of an underlying tissue and surgical mesh.

Anchor 100 is non-cannulated and is constructed from a suitable bioabsorbable material, such as, for example, polylactide, polyglycolide. Anchor 100 is formed from a proprietary biocompatible co-polymer (Lactomer USS L1, Boehringer Ingelheim LR 704 S, or Boehringer Ingelheim LG-857). Anchor may also be constructed from suitable non-bioabsorbable materials, or permanent material, such as, for example, stainless steel, titanium and the like.

Figure 29:
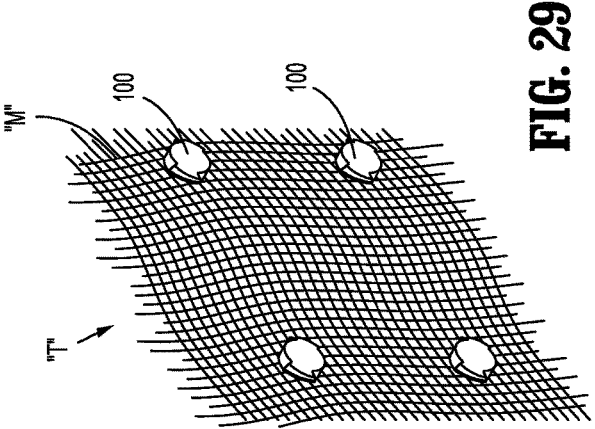
FIG. 29 is an illustration of surgical anchors of the present disclosure fixing a surgical mesh in place.
Figure 31:
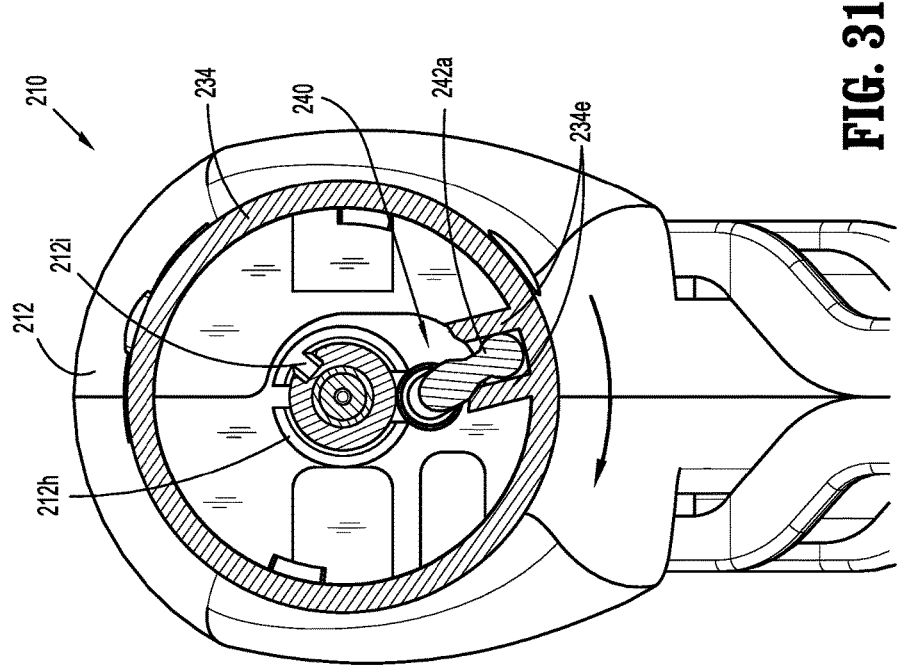
FIG. 31 is a cross-sectional view as taken through section line 31-31 of FIG. 6, illustrating the ferrule being rotated from the lock position to the exchange position.
Figure 30:
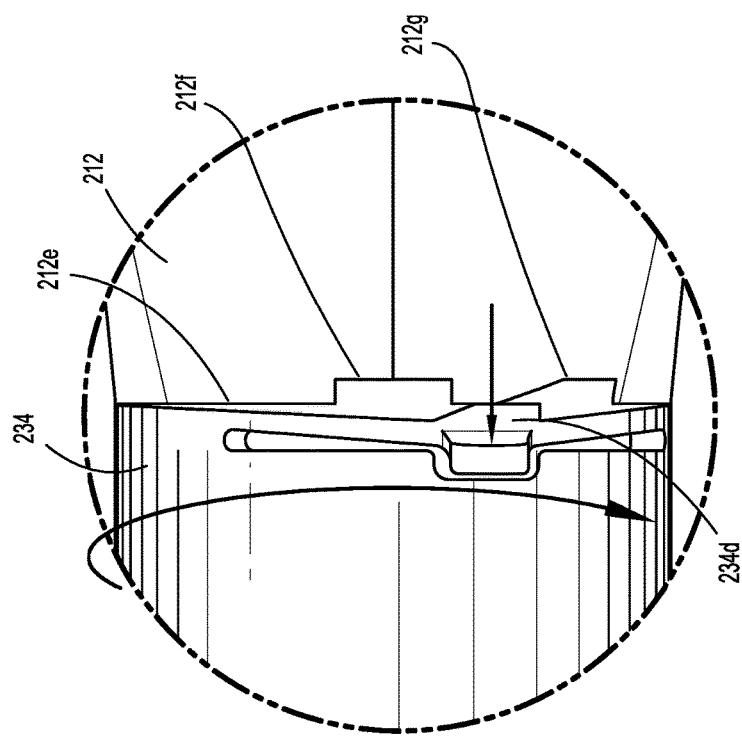
FIG. 30 is an enlarged view of the indicated area of detail of FIG. 6, illustrating the ferrule being rotated from the lock position to an exchange position.
Figure 33:
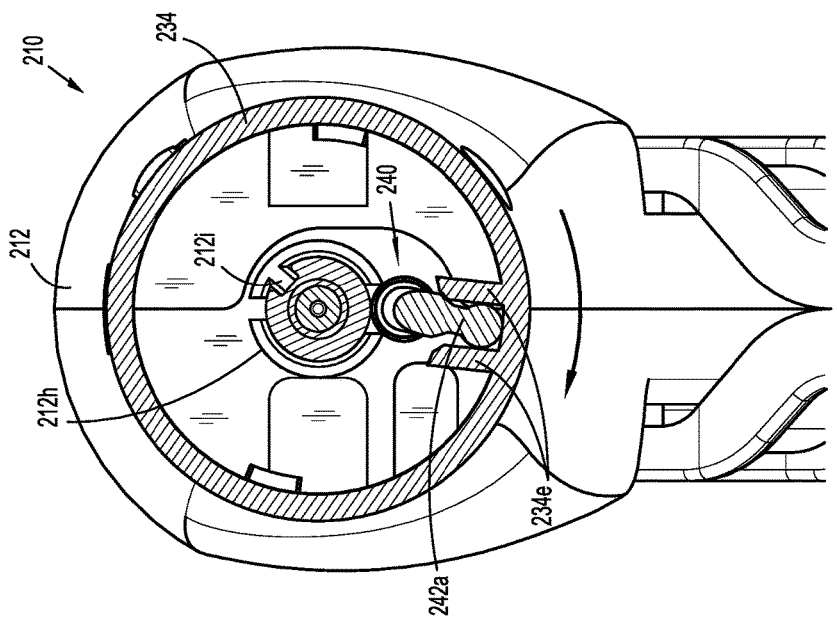
FIG. 33 is a cross-sectional view as taken through section line 33-33 of FIG. 6, illustrating the ferrule rotated to the exchange position.
Figure 32:
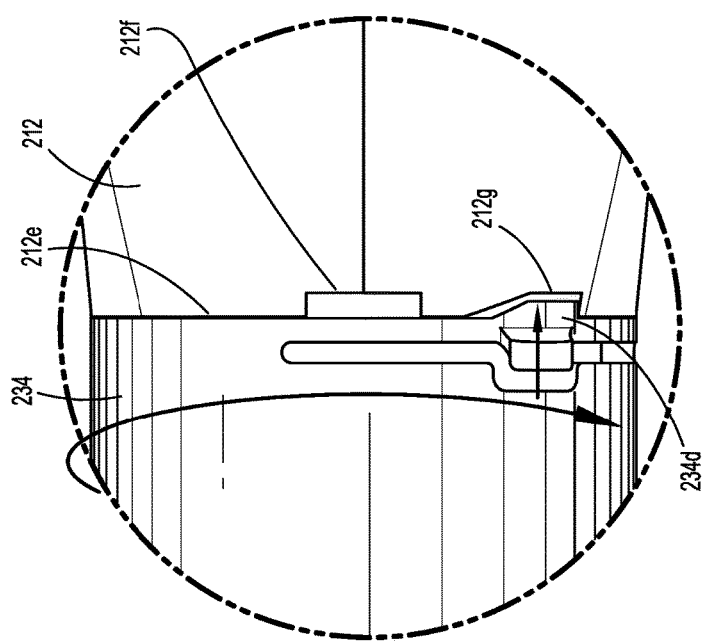
FIG. 32 is an enlarged view of the indicated area of detail of FIG. 6, illustrating the ferrule rotated to the exchange position.
Figure 35:
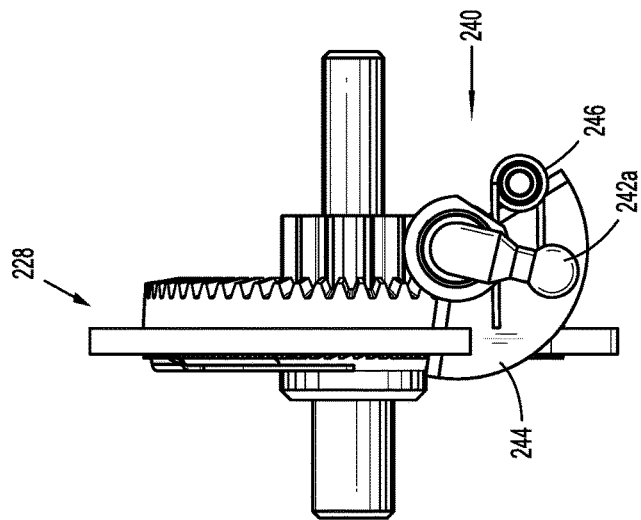
FIG. 35 is a front, plan view of the lock out assembly and the first bevel gear of the gear train of the present disclosure, illustrating the ferrule rotated to the exchange position.
Figure 34:
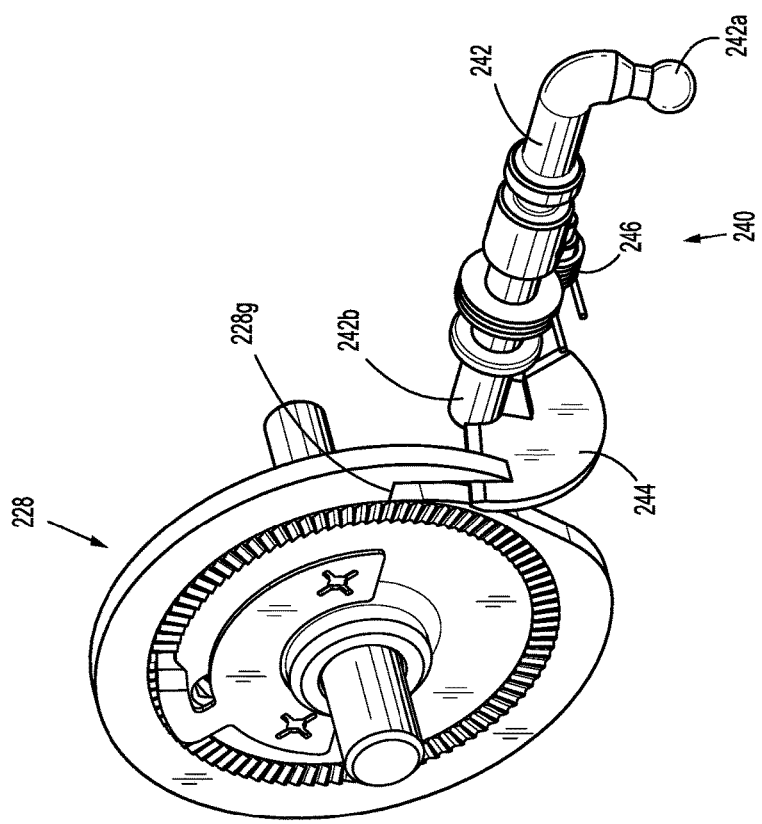
FIG. 34 is a rear, perspective view of the lock out assembly and the first bevel gear of the gear train of the present disclosure, illustrating the ferrule rotated to the exchange position.
Figure 37:
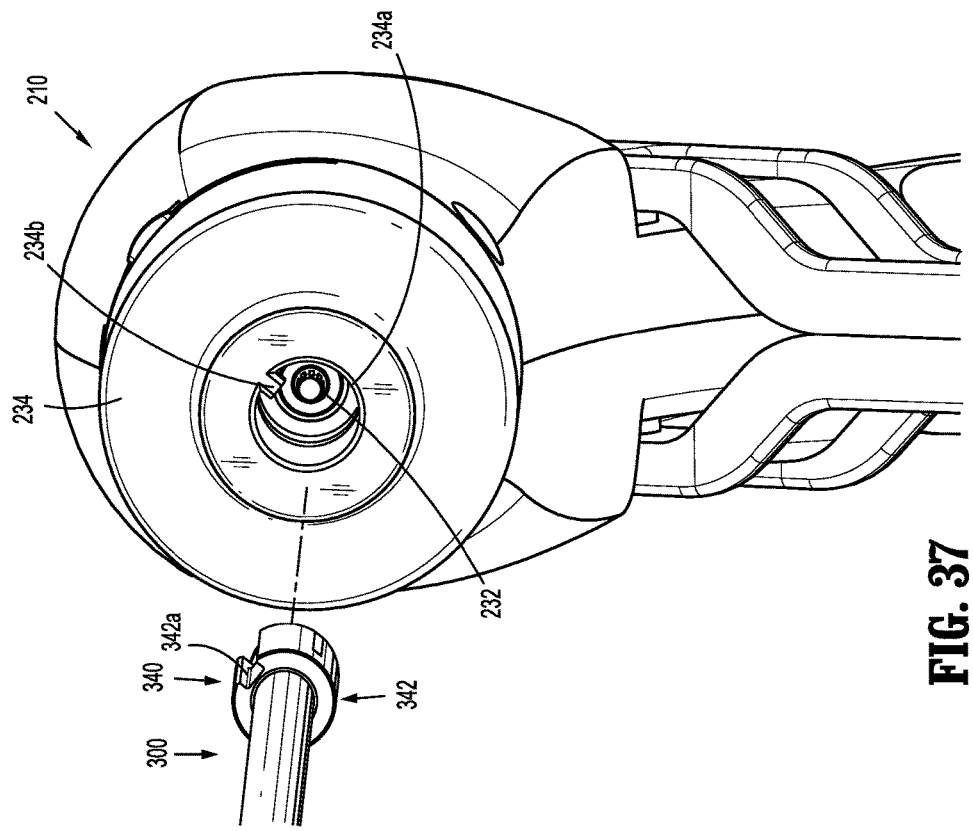
FIG. 37 is a front, perspective view of the handle assembly and the endoscopic assembly, illustrating a connection of the endoscopic assembly to the handle assembly.
Figure 36:
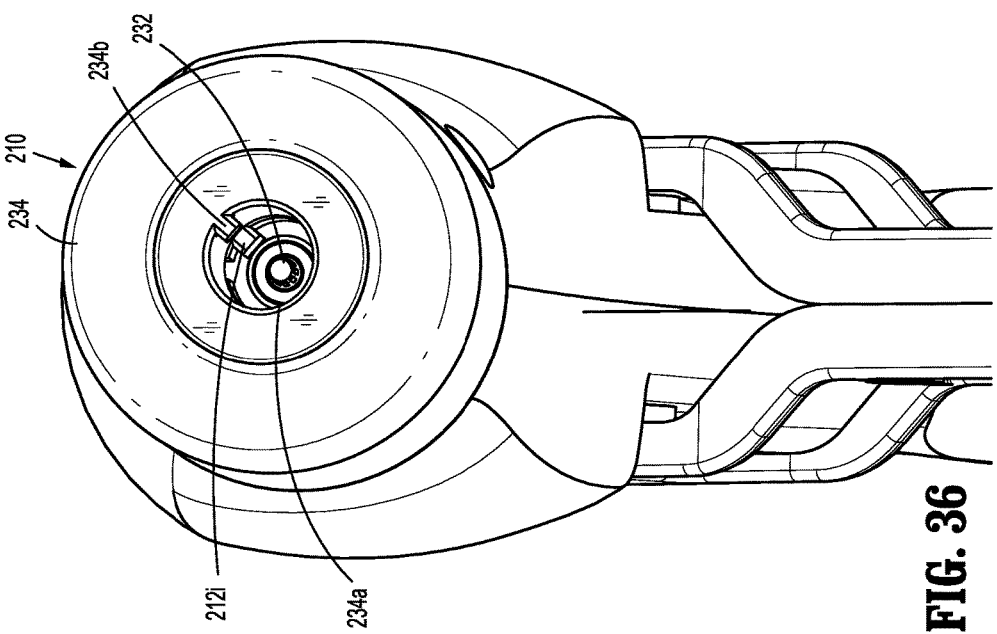
FIG. 36 is a front, perspective view of the handle assembly, illustrating the ferrule rotated to the exchange position.
Figure 39:
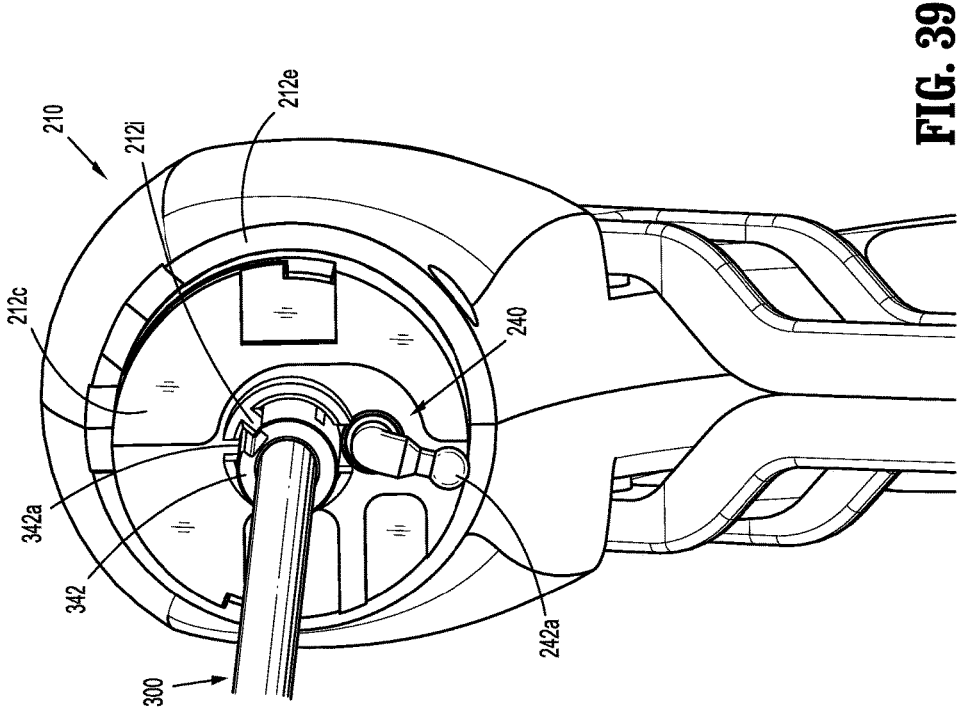
FIG. 39 is a front, perspective view of the handle assembly (with the ferrule removed therefrom) and the endoscopic assembly, illustrating the endoscopic assembly fully connected to the handle assembly.
Figure 38:
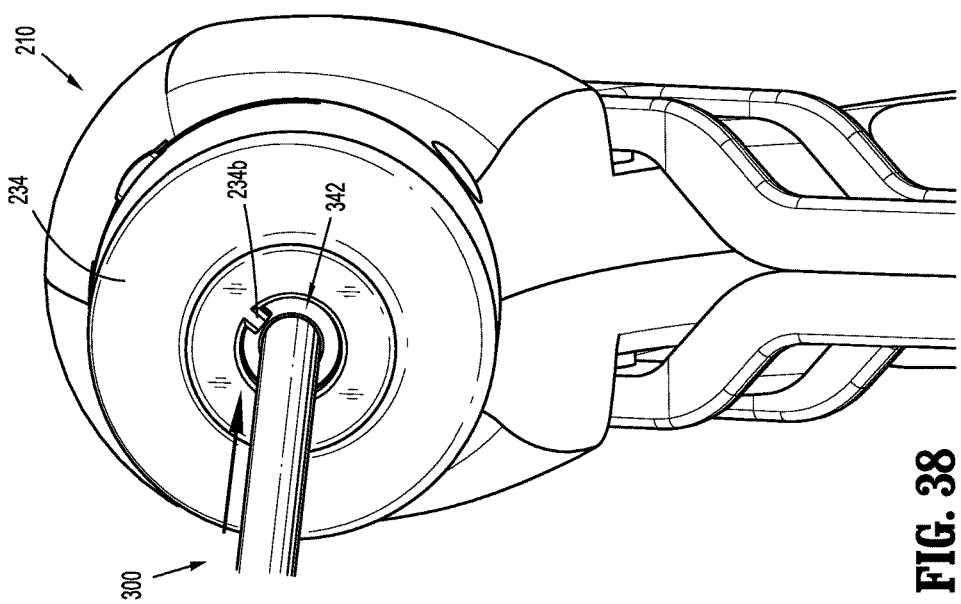
FIG. 38 is a front, perspective view of the handle assembly and the endoscopic assembly, illustrating the endoscopic assembly fully connected to the handle assembly.
Figure 40:
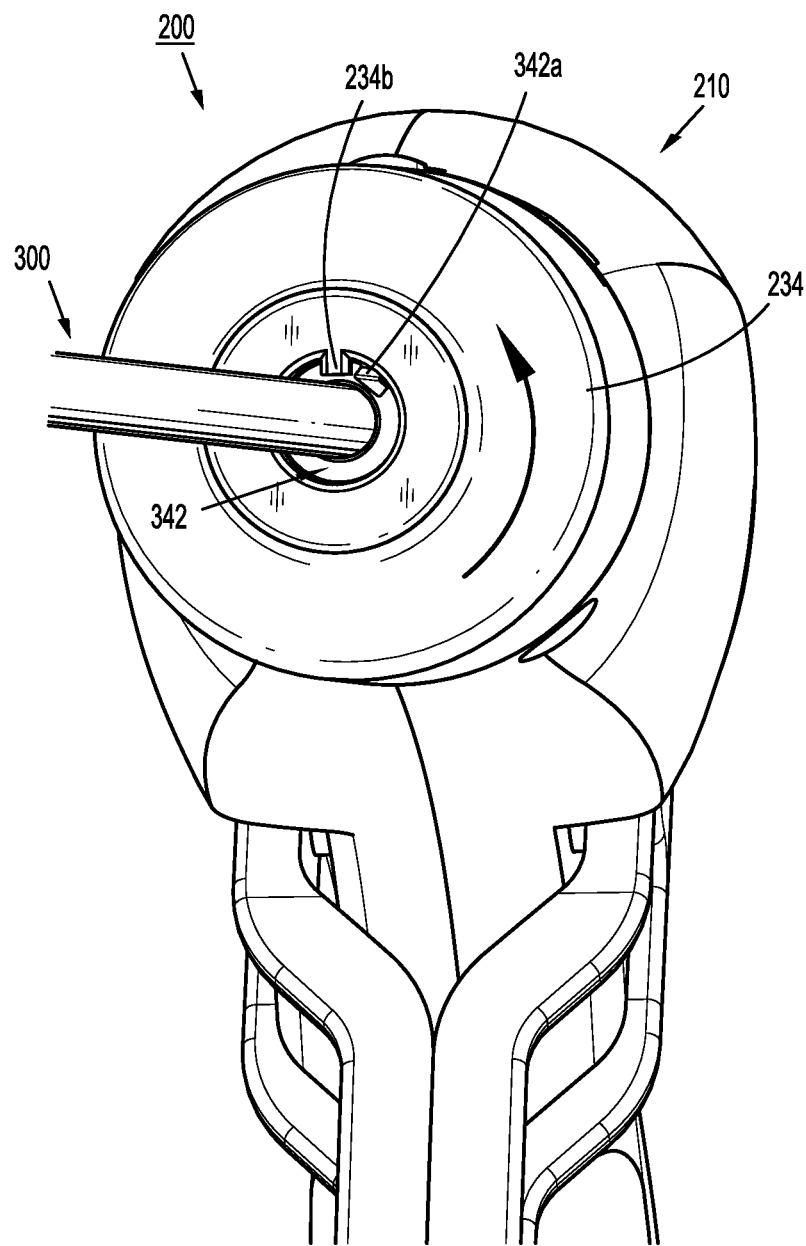
FIG. 40 is a front, perspective view of the handle assembly and the endoscopic assembly, illustrating the endoscopic assembly fully connected to the handle assembly, and illustrating the ferrule being rotated to the lock position.

Turning now to FIGS. 5-47, an endoscopic surgical device, in the form of an endoscopic surgical tack applier or tacker, is shown generally as 200. Tack applier 200 includes a handle assembly 210, and a removable endoscopic assembly 300 (e.g., single use loading unit SULU) extending from handle assembly 210 and configured to store and selectively release or fire a plurality of anchors 100 therefrom and into mesh "M" overlying tissue "T". (FIG. 29).

As illustrated in FIGS. 5-15, handle assembly 210 includes a handle housing 212 formed from a first half-section 212a and a second half section 212b joined to one another. First half-section 212a and second half section 212b of handle housing 212 may be joined to one another using know methods by those of skill in the art, including and not limited to ultrasonic welding, fasteners (i.e., screws) and the like. First half-section 212a and second half section 212b of handle housing 212 are joined to one another such that a fluid-tight seal is provided therebetween.

Handle housing 212 defines a fixed handle portion 216 having a free end 216a. Handle assembly 210 includes a trigger 214 pivotably connected to handle housing 212, at a pivot point disposed within handle housing 212. Trigger 214 includes a free end 214a spaced a distance from fixed handle portion 216 when trigger 214 is in an extended or un-actuated condition. Trigger 214 includes a pivot end 214b extending therefrom and extending into handle housing 212 through a side of handle housing 212.

A fluid-tight seal may be provided between pivot end 214b of trigger 214 and handle housing 212. In accordance with the present disclosure, an X-ring or the like, including an o-ring, etc., (not shown) may be used between pivot end 214b of trigger 214 and handle housing 212.

As illustrated in FIGS. 9-19, handle assembly 210 supports a gear train 220 within handle housing 212. Gear train 220 includes a trigger or drive gear 222 keyed to or non-rotatably connected to pivot end 214b of trigger 214. Drive gear 222 is a two tiered gear including a first drive gear 222a, and a second drive gear 222b. First drive gear 222a may be in the form of a quadrant gear or the like having a plurality of gear teeth $222a_1$ formed along a radial outer edge thereof and extending along an arcuate length of first drive gear 222a. First drive gear 222a includes a stem or stopper 223a extending radially therefrom, at a location proximal of gear teeth $222a_1$. Second drive gear 222b defines a plurality of gear teeth $222b_1$ formed along a radial outer edge thereof.

Gear train 220 further includes a transmission gear assembly 224 pivotably supported in handle housing 212. Transmission gear assembly 224 is a three tiered gear including a first transmission gear 224a, a second transmission gear 224b, and third transmission gear 224c each rotatably supported on a common pivot axis. First transmission gear 224a may be in the form of a pinion gear or the like having a plurality of gear teeth $224a_1$ formed along a radial outer edge thereof and being in meshing engagement with gear teeth $222a_1$ of first drive gear 222a. Second transmission gear 224b may be in the form of a quadrant gear or the like having a plurality of gear teeth $224b_1$ formed along a radial outer edge thereof and extending along an arcuate length of second transmission gear 224b. Third transmission gear 224c may be in the form of a pinion gear or the like having a plurality of gear teeth $224c_1$ formed along a radial outer edge thereof and being in meshing engagement with gear teeth $224b_1$ of second transmission gear 224b.

Figure 10:
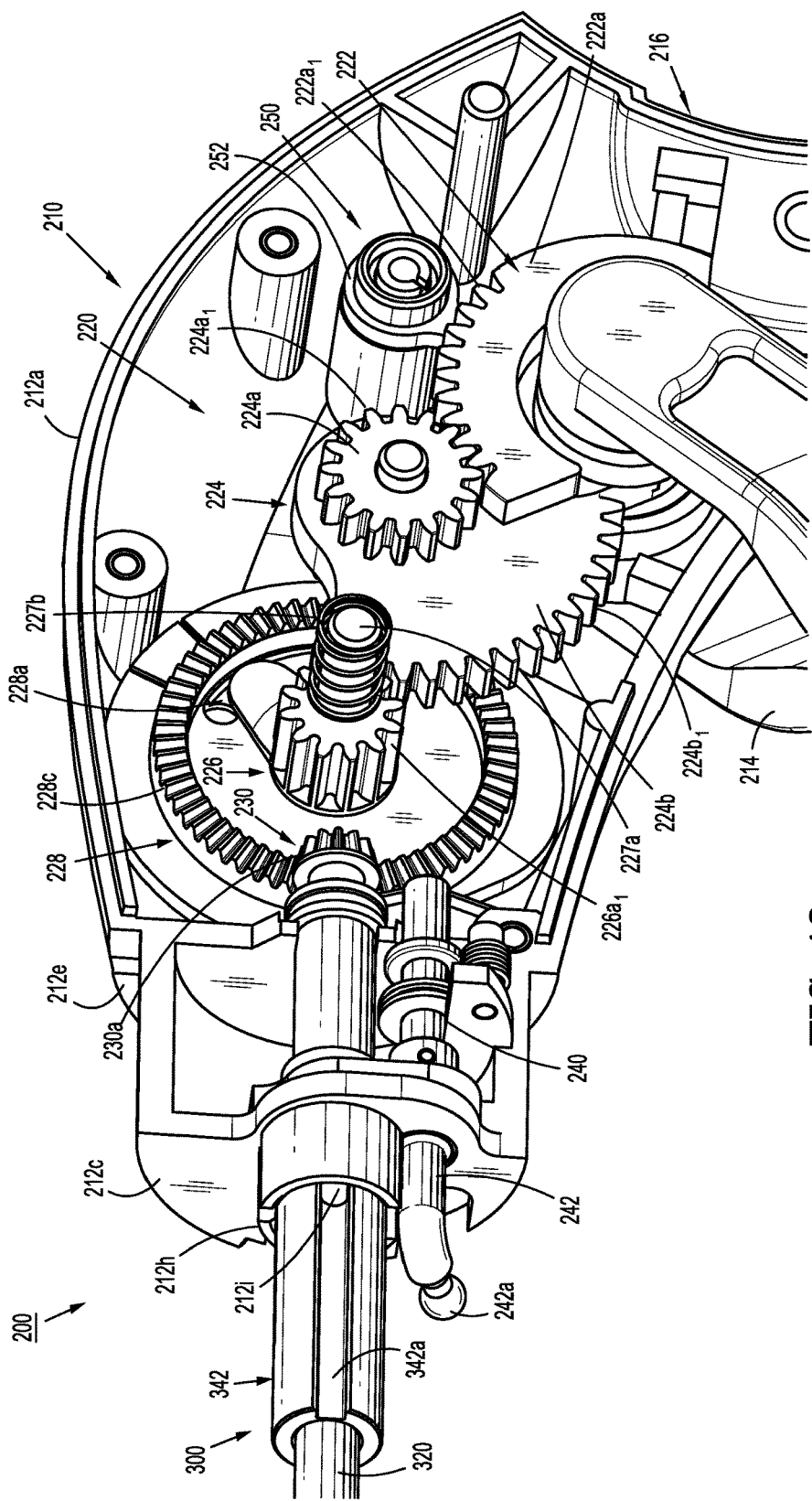
FIG. 10 is a left, front, perspective view of the surgical device of FIGS. 5-8, illustrating a second half-section of the handle assembly removed therefrom.
Figure 11:
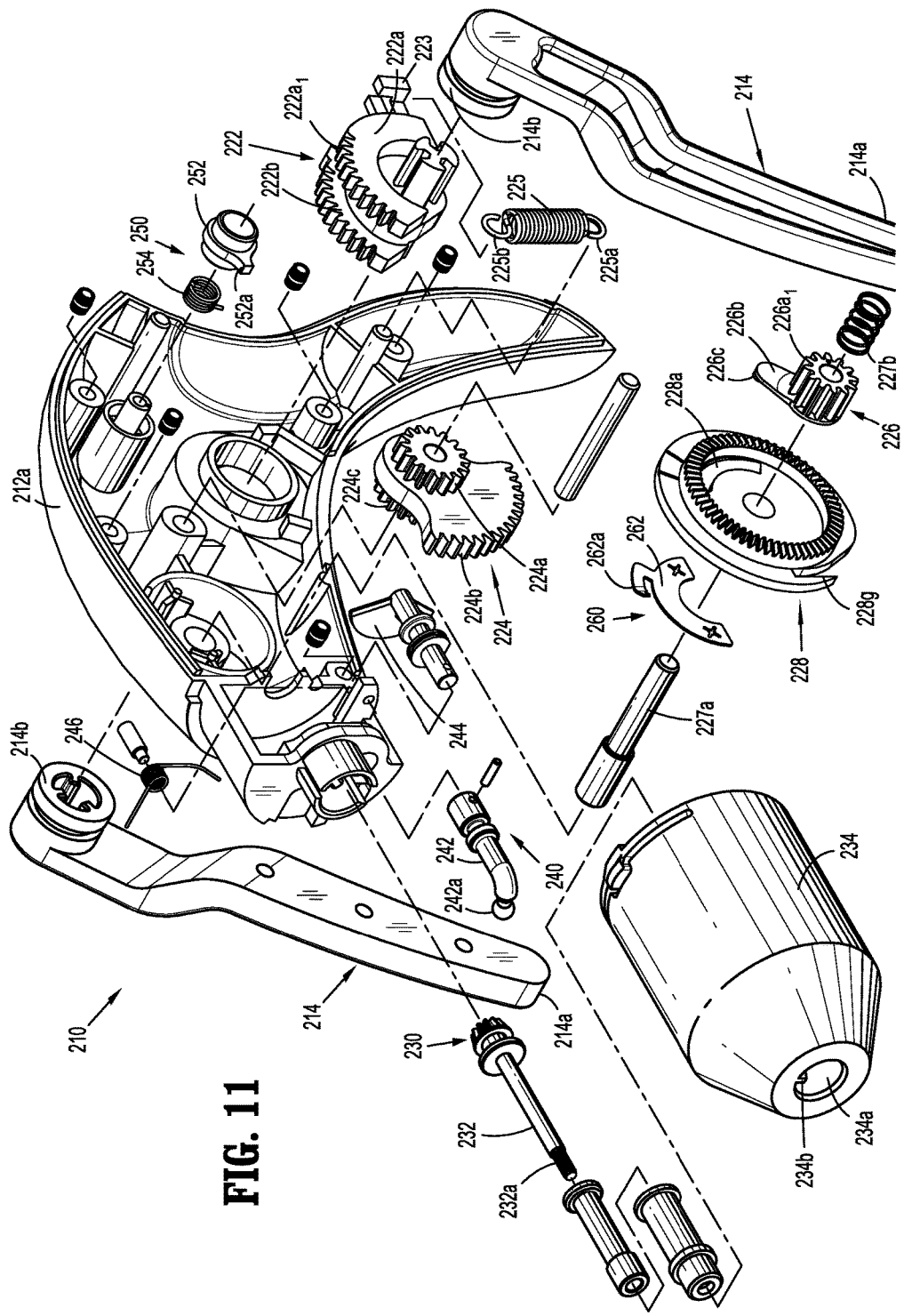
FIG. 11 is a left, front, perspective view, with parts separated, of the surgical device of FIGS. 5-8, illustrating a second half-section of the handle assembly removed therefrom.
Figure 12:
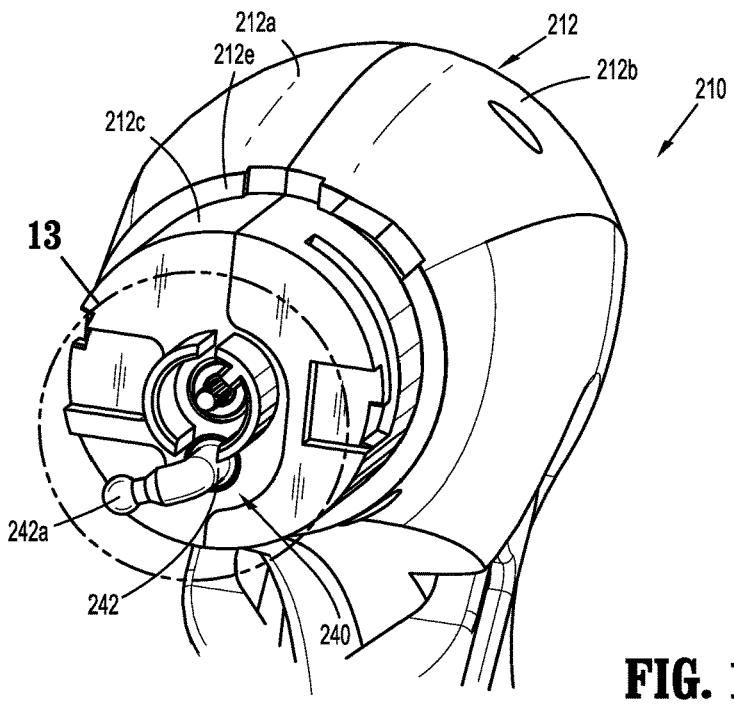
FIG. 12 is a front, perspective view of the surgical device of FIGS. 5-8, illustrating a ferrule removed therefrom.
Figure 13:
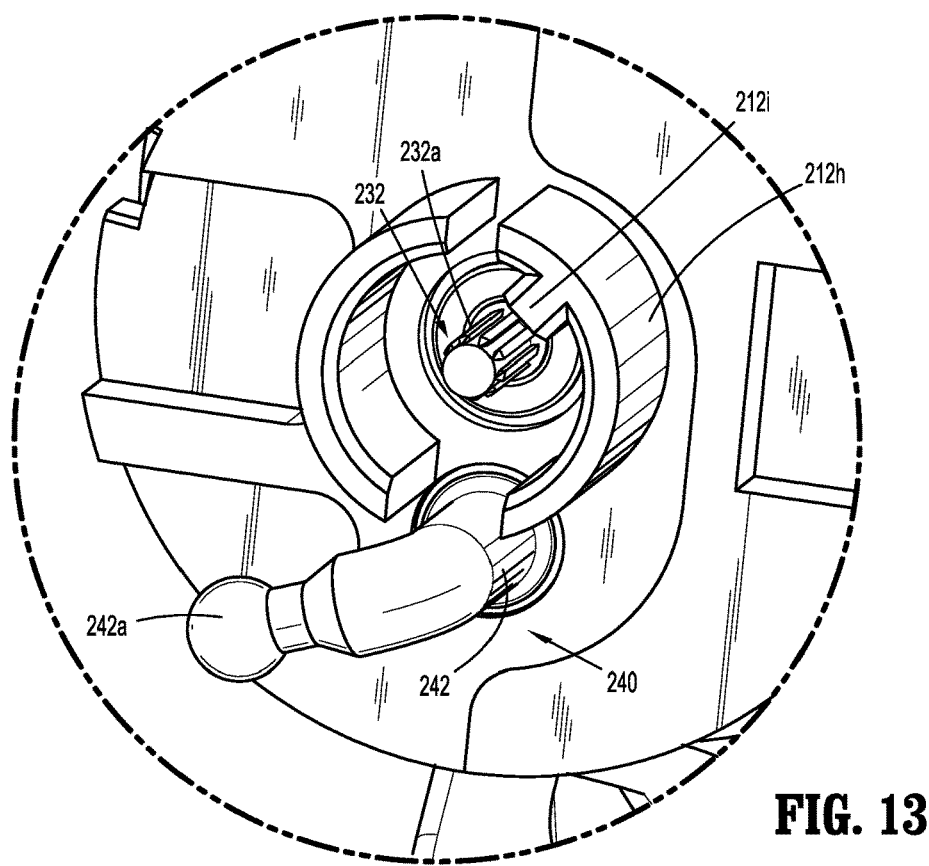
FIG. 13 is an enlarged view of the indicated area of detail of FIG. 12.

Gear train 220 also includes a clutch gear 226 pivotably and slidably supported on a pivot axis 227a in handle housing 212. Clutch gear 226 may be in the form of a pinion gear or the like having a plurality of gear teeth $226a_1$ formed along a radial outer edge thereof and being in meshing engagement with gear teeth $224b_1$ of second transmission gear 224b. Clutch gear 226 is biased into meshing engagement with second transmission gear 224b by a biasing member 227b (FIGS. 10 and 11). Clutch gear 226 includes an arm 226b extending radially therefrom, and a cam or ramp 226c (FIG. 11) extending/projecting from arm 226b. Cam 226c includes a front end having a height defining a shoulder, and a tail end tapering into arm 226b.

Gear train 220 further includes a first bevel gear 228 pivotably and slidably supported on pivot axis 227a in handle housing 212. First bevel gear 228 may be in the form of a crown gear or the like. First bevel gear 228 is operatively engaged/associated with clutch gear 226. First bevel gear 228 defines an arcuate slot 228a formed in first face 228d thereof for selectively receiving and engaging cam 226c of clutch gear 226. Slot 228a includes a front end wall configured to engage the front end of cam 226c of clutch gear 226, and tapers along a length thereof to be flush with the first face of first bevel gear 228.

In operation, as trigger 214 of tacker 200 is actuated, trigger 214 causes drive gear 222 to be rotated, in a first direction. As drive gear 222 is rotated in the first direction, drive gear 222 causes first transmission gear 224a and second transmission gear 224b to be rotated, in a first direction, about the pivot axis thereof. As second transmission gear 224b is rotated in the first direction, second transmission gear 224b causes clutch gear 226 to be rotated, in a first direction, about a pivot axis thereof.

As clutch gear 226 is rotated in the first direction, the front end of cam 226c of clutch gear 226 is rotated in a first direction until the front end of cam 226c engages or contacts the front end wall of slot 228a of first bevel gear 228. After the front end of cam 226c of clutch gear 226 engages or contacts the front end wall of slot 228a of first bevel gear 228, continued rotation of clutch gear 226, in the first direction, results in concomitant rotation of first bevel gear 228 in a first direction. At this point, first bevel gear 228 continues to rotate in the first direction so long as trigger 214 is being actuated to a closed or fully actuated condition.

When actuation of trigger 214 is stopped, either prior to complete actuation or following complete actuation, rotation of first bevel gear 228, in the first direction, is also stopped. Upon the completion of a partial or complete actuation of trigger 214 and a release thereof, trigger 214 causes drive gear 222 to be rotated, in a second direction (opposite the first direction). As drive gear 222 is rotated in the second direction, drive gear 222 causes first transmission gear 224a and second transmission gear 224b to be rotated, in a second direction, about the pivot axis thereof. As second transmission gear 224b is rotated in the second direction, second transmission gear 224b causes clutch gear 226 to be rotated, in a second direction, about pivot axis 227a. As clutch gear 226 is rotated in the second direction, the tail end of cam 226c thereof slides along slot 228a of first bevel gear 228, and, if the rotation in the second direction is sufficient, slides out of slot 228a of first bevel gear 228 and along first face 228d of first bevel gear 228. As cam 226c of clutch gear 226 slides along slot 228a of first bevel gear 228, clutch gear 226 slides axially along pivot axis 227a and compresses biasing member 227b.

If trigger 214 was fully actuated, a complete release of trigger 214, will result in clutch gear 226 making a complete revolution, in the second direction, until the front end of cam 226c of clutch gear 226 clears the front end wall of slot 228b of first bevel gear 228 to thereby re-enter slot 228b of first bevel gear 228. Specifically, as the front end of cam 226c of clutch gear 226 clears the front end wall of slot 228b of first bevel gear 228, biasing member 227b forces clutch gear 226 axially along pivot axis 227a and cam 226c of clutch gear 226 back into slot 228b of first bevel gear 228.

Figures 26, 27:
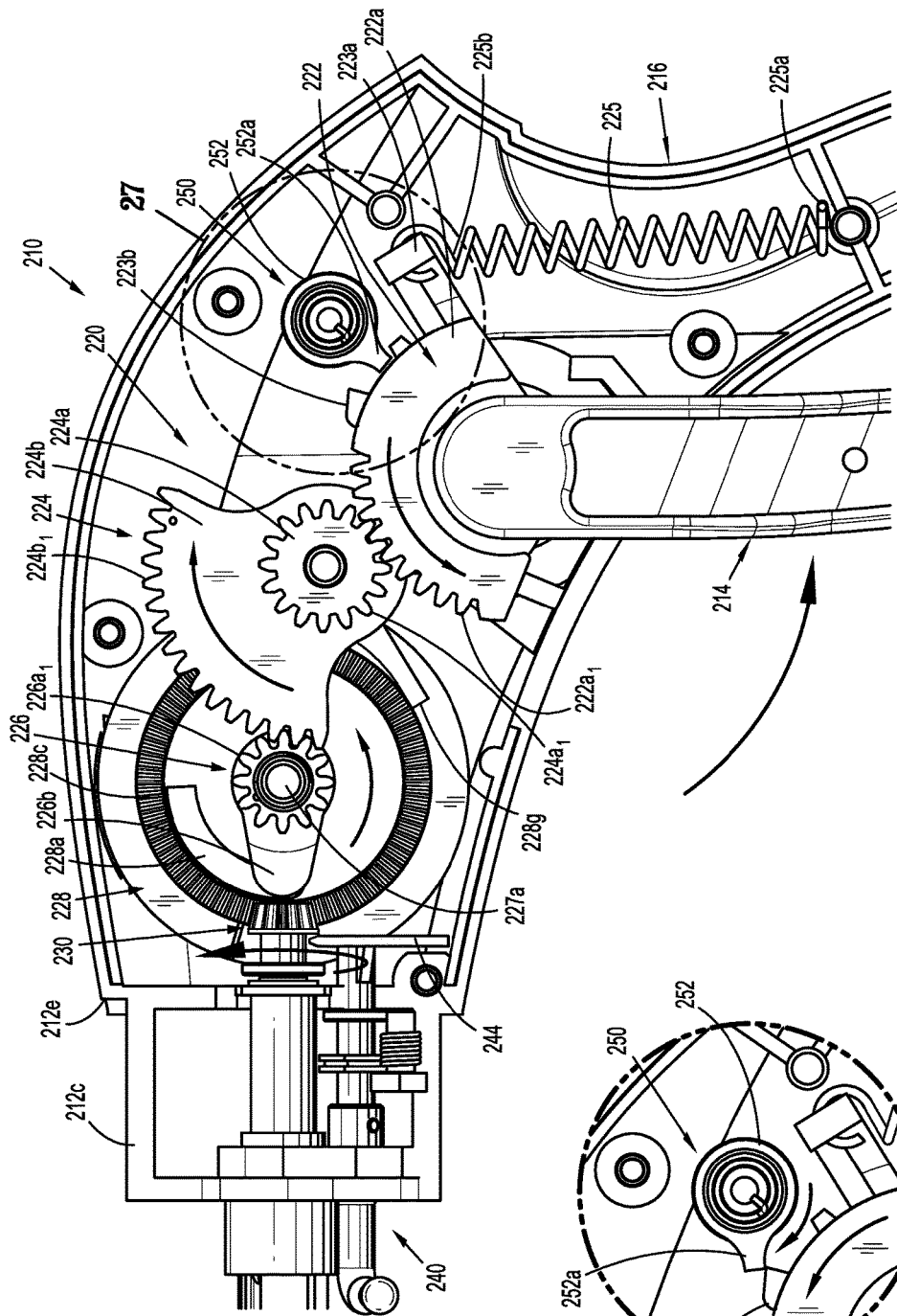
FIG. 26 is a side elevational view of the handle assembly, with a housing half-section removed therefrom, illustrating the handle assembly during a firing stroke of the endoscopic surgical device.
FIG. 27 is an enlarged view of the indicated area of detail of FIG. 26.
Figure 28:
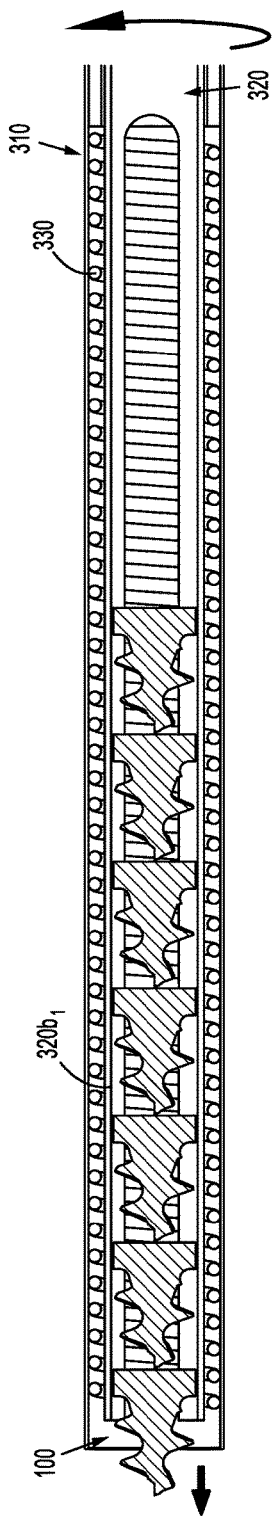
FIG. 28 is a cross-sectional view of the distal end portion of the endoscopic assembly, as taken through section line 28-28 of FIG. 8, illustrating the endoscopic assembly during a firing stroke of the endoscopic surgical device.

As illustrated in FIGS. 11 and 26, handle assembly 210 includes a biasing member 225 configured for maintaining trigger 214 in an extended or un-actuated position. Biasing member 225 is also configured to have a spring constant sufficient to return trigger 214 to the un-actuated position following a partial or complete actuation of trigger 214. Biasing member 225 includes a first end 225a fixedly connected in handle housing 212 and a second end 225b connected to stem 223a extending from first drive gear 222a.

With reference to FIGS. 9-11, 26 and 27, handle assembly 210 includes an audible/tactile feedback mechanism 250 supported within handle housing 212 and in operative association with drive gear 222. Specifically, audible/tactile feedback mechanism 250 includes a dial 252 rotatably supported in handle housing 212. Dial 252 includes a tooth 252a extending therefrom. Dial 252 is spring biased to a home position. Audible/tactile feedback mechanism 250 further includes a tooth or stem 223b extending from second drive gear 222b. In operation, as trigger 214 is actuated and second drive gear 222b rotated, stem 223b of second drive gear 222b contacts tooth 252a of dial 252 causing dial 252 to rotate against the bias of a spring member 254. When stem 223b of second drive gear 222b clears tooth 252a of dial 252, dial 252 is returned to or snapped back to the home position thereof due to the bias of spring member 254. When dial 252 is snapped back to the home position thereof, dial 252 creates an audible and/or tactile response.

Figure 9:
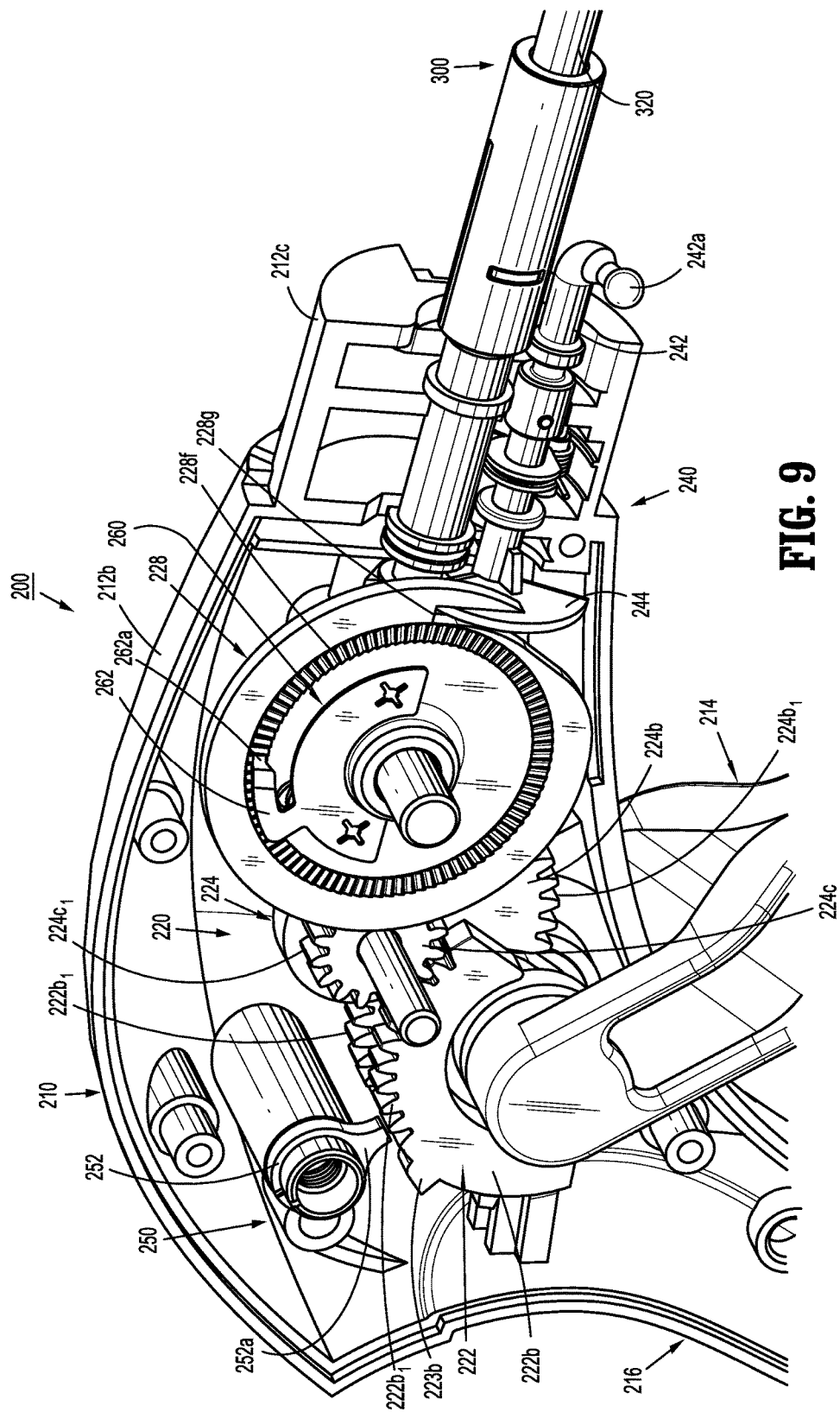
FIG. 9 is a right, front, perspective view of the surgical device of FIGS. 5-8, illustrating a first half-section of the handle assembly removed therefrom.

As shown in FIGS. 9, 11, 18 and 19, handle assembly 210 of tack applier 200 is provided with a ratchet mechanism 260 which is configured to inhibit or prevent inner tube 320 (FIGS. 20, 24 and 25) from backing-out or reversing after anchor 100 has been at least partially driven into tissue. Ratchet mechanism 260 includes, as seen in FIGS. 9 and 11, a series of ratchet teeth 228f formed on a rear or second face of first bevel gear 228.

Ratchet mechanism 260 further includes a spring clip 262 secured within handle assembly 210. Spring clip 262 includes a resilient finger 262a configured for engagement with ratchet teeth 228f formed on rear surface of first bevel gear 228.

In operation, resilient finger 262a of spring clip 262 engages with ratchet teeth 228f of first bevel gear 228 in such a manner that as first bevel gear 228 is rotated, in a first direction, resilient finger 262a of spring clip 262 cams over ratchet teeth 228f and permits rotation of first bevel gear 228. Also, if first bevel gear 228 starts to rotate in a second direction (opposite to the first direction), resilient finger 262a of spring clip 262 stops along ratchet teeth 228f thereby preventing or inhibiting first bevel gear 228 from rotating in the second direction. As such, any reverse rotation or "backing-out" of anchor 100 or inner tube 320 of endoscopic assembly 300 (tending to cause first bevel gear 228 to rotate in the second direction), during a driving or firing stroke, is inhibited or prevented.

With reference to FIGS. 10, 11 and 26, handle assembly 210 further includes a second or pinion-bevel gear 230 rotatably supported in a distal end of handle housing 212. Pinion-bevel gear 230 includes gear teeth 230a operatively engaged or meshed with gear teeth 228c formed on the front face of first bevel gear 228. Pinion-bevel gear 230 is non-rotatably secured to a drive shaft 232 extending distally from handle housing 212. Drive shaft 232 is configured and dimensioned to engage an inner connector member 344 of endoscopic assembly 300 (FIGS. 20 and 21). In an embodiment, drive shaft 232 defines a plurality of axially extending ribs 232a at a distal end thereof.

In operation, upon squeezing of trigger 214, gear train 220 causes pinion-bevel gear 230 to rotate in a first direction. As pinion-bevel gear 230 is rotated in the first direction, pinion-bevel gear 230 transmits the rotation to inner tube 320 of endoscopic assembly 300.

With reference to FIGS. 5-16, handle assembly 210 includes a ferrule or collar 234 rotatably and removably supported on handle housing 212. Ferrule 234 defines a distal opening 234a that is axially aligned with drive shaft 232. Ferrule 234 includes a stopper or tooth 234b extending radially into distal opening 234a.

Figure 14:
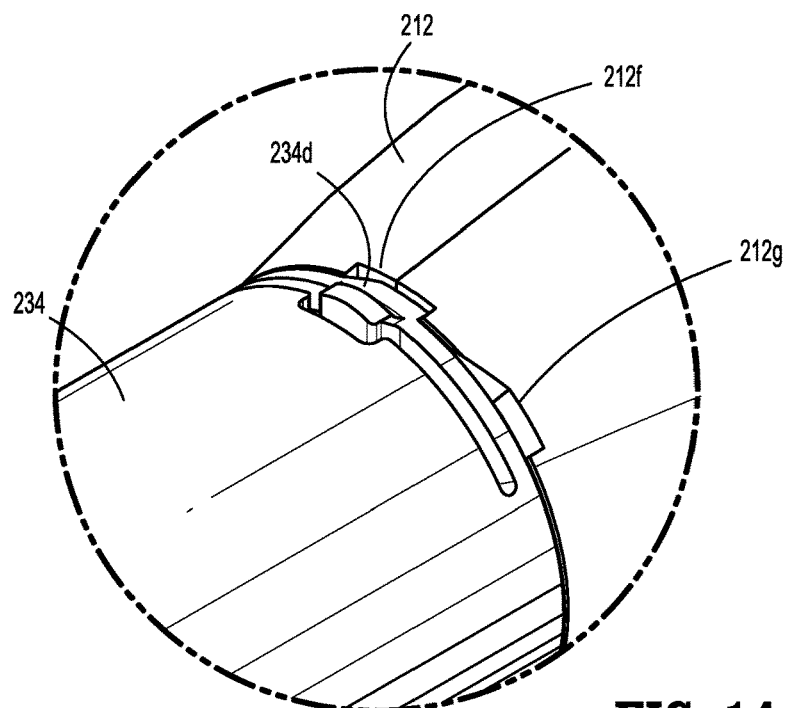
FIG. 14 is an enlarged view of the indicated area of detail of FIG. 5, illustrating the ferrule in a lock position.
Figure 15:
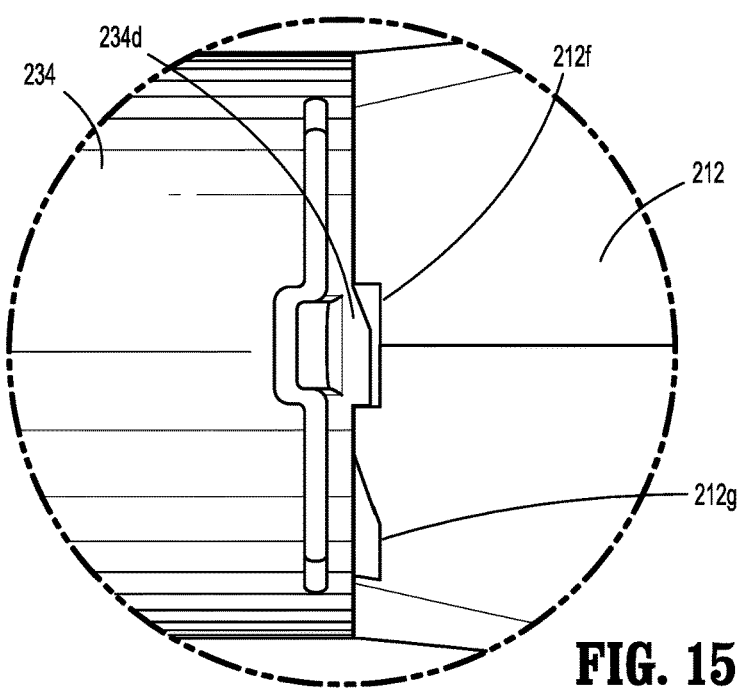
FIG. 15 is an enlarged view of the indicated area of detail of FIG. 6, illustrating the ferrule in the lock position.
Figure 42:
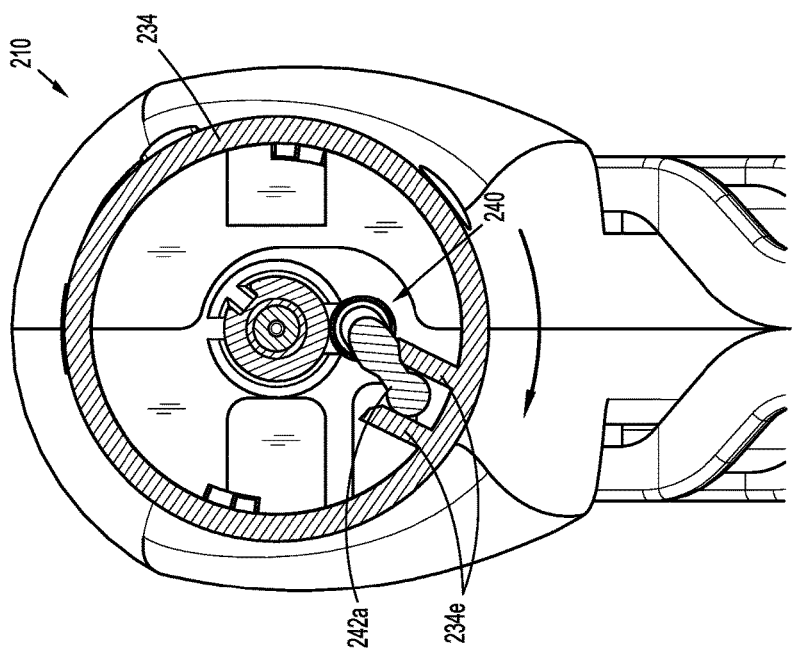
FIG. 42 is a cross-sectional view as taken through section line 42-42 of FIG. 6, illustrating the ferrule rotated to the release position.
Figure 41:
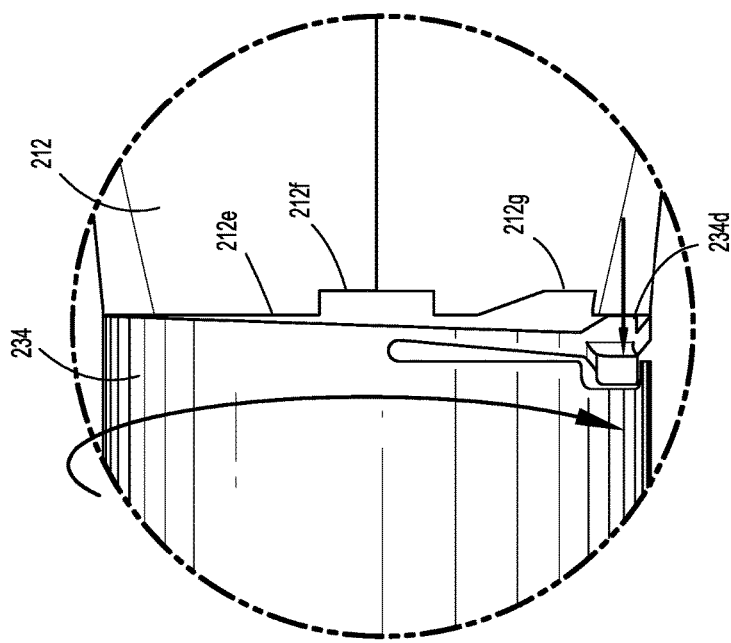
FIG. 41 is an enlarged view of the indicated area of detail of FIG. 6, illustrating the ferrule rotated to a release position.
Figure 44:
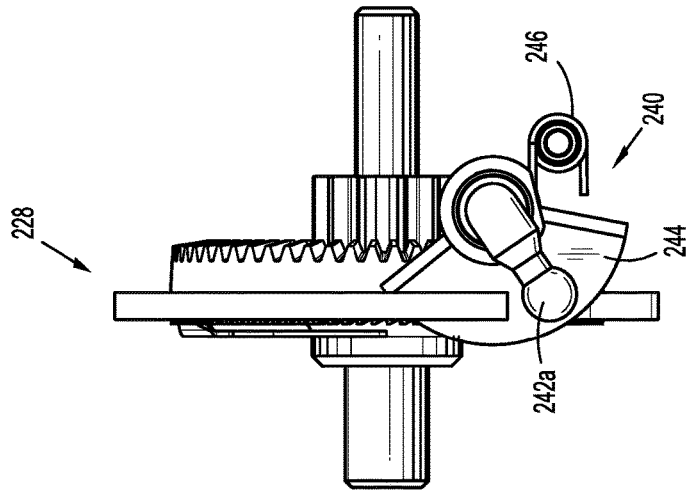
FIG. 44 is a front, plan view of the lock out assembly and the first bevel gear of the gear train of the present disclosure, illustrating the ferrule rotated to the release position.
Figure 43:
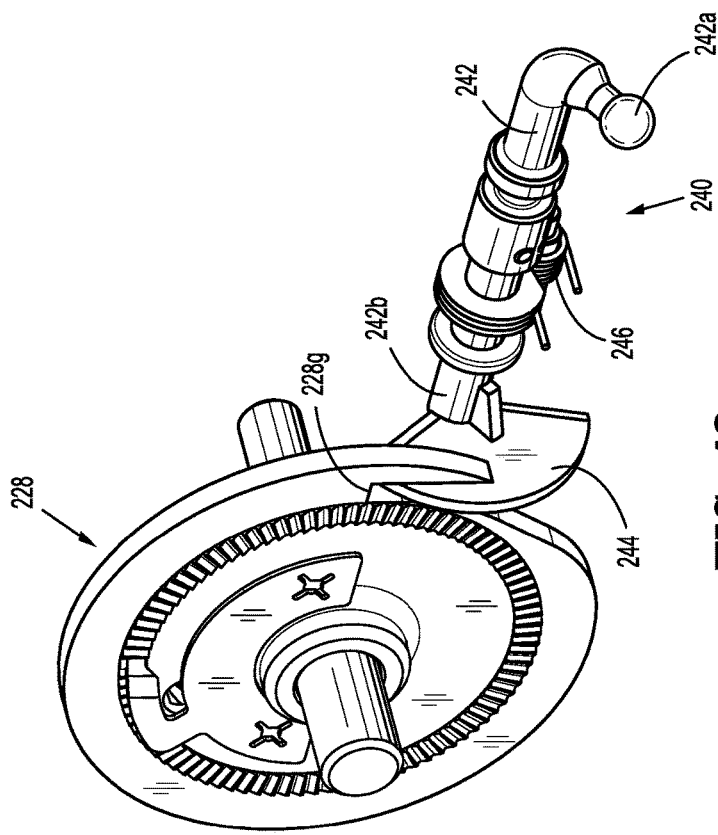
FIG. 43 is a rear, perspective view of the lock out assembly and the first bevel gear of the gear train of the present disclosure, illustrating the ferrule rotated to the release position.

Ferrule 234 is rotatable between a lock position (anchor retaining/advancing assembly 300 is locked to handle assembly 212, and tacker 200 is ready to fire, FIGS. 14-16); an exchange position (anchor retaining/advancing assembly 300 can be connected/disconnected to/from handle assembly 212, and tacker 200 can not be fired, FIGS. 30-33); and a ferrule release position (ferrule 234 can be removed from handle housing 212, and handle housing 212 may be cleaned or sterilized, FIGS. 41 and 42).

Figure 45:
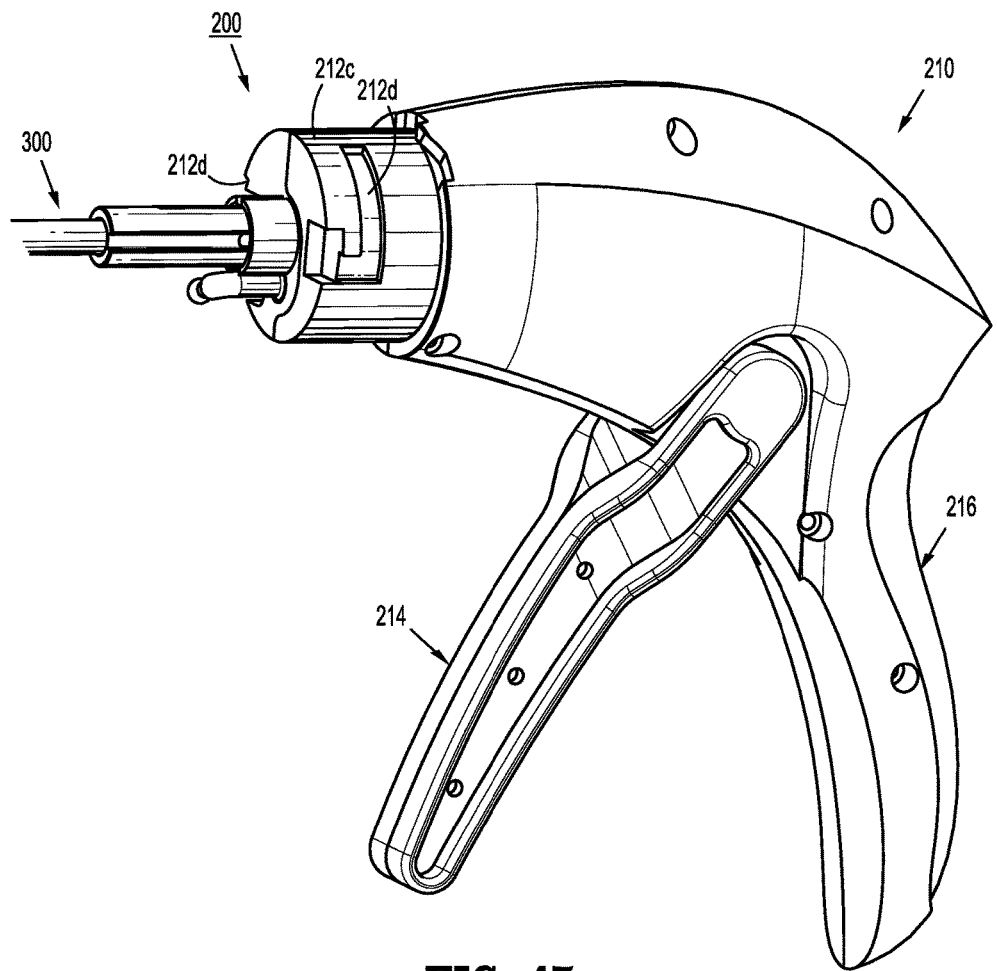
FIG. 45 is a front, perspective view of the surgical device of FIGS. 5-8, illustrating a ferrule removed therefrom.
Figure 46:
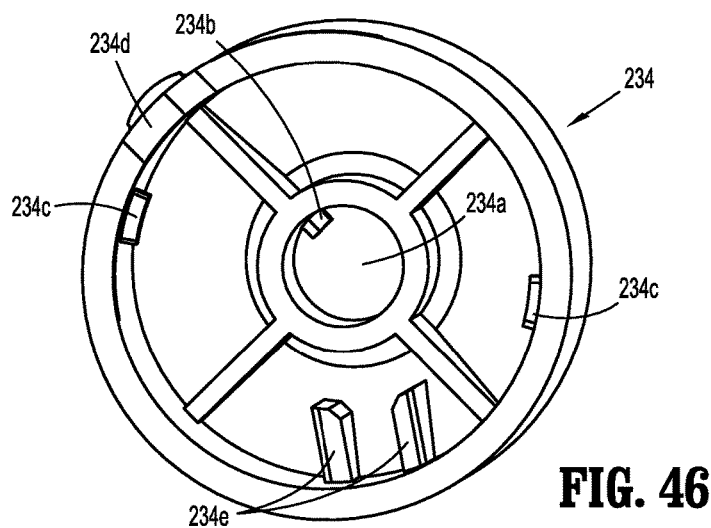
FIG. 46 is a rear, perspective view of the ferrule, illustrating internal features thereof.
Figure 47:
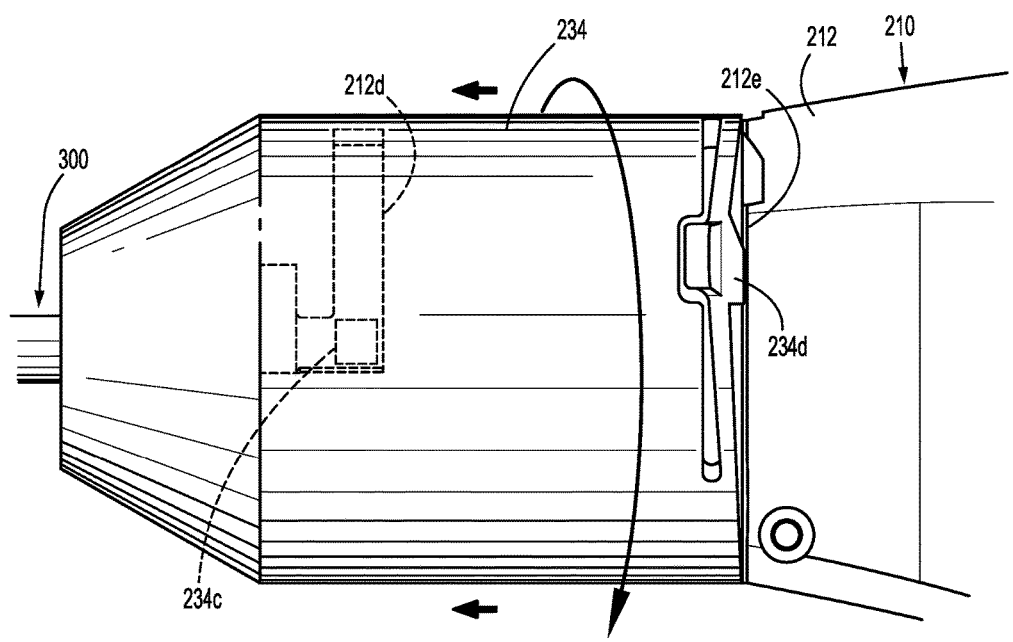
FIG. 47 is an enlarged, plan view (with portions in phantom) illustrating the ferrule in the release position relative to a handle housing of the handle assembly.

Handle housing 212 and ferrule 234, as illustrated in FIGS. 45-47, may include complementary inter-engaging features and/or structures which lock or fix a position/orientation of ferrule 234 relative to handle housing 212. Ferrule 234 includes opposed radially inwardly extending nubs 234c and handle housing 212 includes a pair of L-shaped slots 212d formed in an outer surface of a nose 212c thereof. Housing defines an annular shoulder 212e around a proximal end of nose 212c. Shoulder 212e defines a pair of recesses 212f, 212g formed in a distal face of shoulder 212e.

Turning now to FIGS. 10, 12, 13 and 36-40, nose 212c of handle housing 212 includes a distally extending annular wall 212h surrounding the distal end of drive shaft 232. Annular wall 212h includes a tooth 212i projecting radially inward therefrom. When ferrule 234 is in the exchange position, stopper or tooth 234b of ferrule 234 is radially aligned with tooth 212i of annular wall 212h. When ferrule 234 is in the lock position, stopper or tooth 234b of ferrule 234 is radially out of alignment with tooth 212i of annular wall 212h.

Ferrule 234 includes a second tooth 234d projecting from a proximal surface thereof. Tooth 234d is configured to engage a selected one of recesses 212f, 212g of housing 212 as ferrule 234 is rotated relative to housing 212. Tooth 234d is biased to project from proximal end of ferrule 234.

As shown in FIGS. 9-13, 16-19, 30-35 and 42-44, handle assembly 210 includes a safety lock assembly 240 supported on handle housing 212 and being configured to permit and inhibit actuation of trigger 214, and for effectuating a loading/retention and a release/removal of endoscopic assembly 300 to handle housing 212. Safety lock assembly 240 is in operative association with ferrule 234 and is actuatable upon a rotation of ferrule 234 relative to handle housing 212. Safety lock assembly 240 includes a lock pin 242 slidably supported in and projecting distally from handle housing 212. Pin 242 includes a transverse head 242a extending therefrom. Head 242a of lock pin 242 is operatively disposed within or between internal walls 234e (FIGS. 16, 31, 33, 42 and 46) provided in ferrule 234.

Safety lock assembly 240 includes a lock plate 244 supported on a proximal end 242b of lock pin 242. Lock plate 244 has a generally pie-shaped profile. In use, lock plate 244 is caused to be rotated as lock pin 242 is rotated, due to internal walls 234e of ferrule 234 acting on head 242a of pin 242 as ferrule 234 is rotated relative to handle housing 212. In operation, when ferrule 234 is rotated to the exchange position or the ready-to-fire position, with trigger 214 in a fully un-actuated position, lock plate 244 is rotated into a radial slot 228g formed in first bevel gear 228, thereby preventing first bevel gear 228 from rotating. Moreover, when ferrule 234 is rotated to the lock position, lock plate 244 is rotated out of radial slot 228g of first bevel gear 228, thereby allowing first bevel gear 228 to rotate.

Safety lock assembly 240 further includes a biasing member 246 configured to bias head 242a of pin 242 and lock plate 244 to the rotated lock position.

Turning now to FIGS. 5, 8-10 and 20-25, as illustrated therein, endoscopic assembly 300 includes an outer tube 310, an inner tube 320 rotatably disposed within outer tube 310, a guide coil or spring 330 disposed between outer tube 310 and inner tube 320, a plurality of anchors 100 loaded within inner tube 310, and a connector 340 supported at a proximal end of outer tube 310 and inner tube 320.

Outer tube 310 of endoscopic assembly 300 includes a proximal end 310a and a distal end 310b, and defines a lumen 310c therethrough. As described briefly above, endoscopic assembly 300 further includes a guide coil or spring 330 fixedly disposed within at least a distal portion of outer tube 310.

Endoscopic assembly 300 also includes an inner tube 320 rotatably disposed within coil 330. Inner tube 320 includes a proximal end portion 320a and a splined distal end portion 320b, and defines a lumen 320c therethrough.

Distal end portion 320b of inner tube 320 is slotted, defining a pair of opposed tines $320b_1$ and a pair of opposed channels $320b_2$. Distal end portion 320b of inner tube 320 is capable of accepting a plurality of anchors 100 within inner tube 320. In particular, anchors 100 are loaded into endoscopic assembly 300 such that the pair of opposing threaded sections 112a, 112b of anchors 100 extend through respective channels $320b_2$ of distal end portion 320b of inner tube 320 and are slidably disposed within the groove of coil 330, and the pair of tines $320b_1$ of distal end portion 320b of inner tube 320 are disposed within the pair of slotted sections 116a, 116b of anchors 100.

In use, as inner tube 320 is rotated, about its longitudinal axis, with respect to coil 330, the pair of tines $320b_1$ of inner tube 320 transmit the rotation to anchors 100 and advance anchors 100 distally owing to head threads 114a, 114b of anchors 100 engaging with coil 330.

As illustrated specifically in FIGS. 20 and 21, endoscopic assembly 300 includes a connector 340 having an outer connector member 342 non-rotatably connected to proximal end 310a of outer tube 310, and an inner connector member 344 non-rotatably connected to proximal end 320a of inner tube 320. Inner connector member 344 is nested within outer connector member 342. Outer connector member 342 is substantially cylindrical and defines at least one longitudinally extending outer radial groove 342a that extends through a proximal end thereof, and at least one longitudinally extending inner groove 342b. Outer connector member 342 is sized and shaped to be inserted into distal opening 234a of ferrule 234 of handle assembly 210 and into annular wall 212h of nose 212c of handle housing 212.

Inner connector member 344 is substantially cylindrical and defines at least one longitudinally extending inner rib 344a projecting radially into a lumen thereof.

In order to connect endoscopic assembly 300 to handle assembly 210, with ferrule 234 in the exchange position, outer radial groove 342a of outer connector member 342 is first aligned with stopper or tooth 234b of ferrule 234 and with tooth 212i of annular wall 212h of nose 212c. Then, outer connector member 342 is fully inserted into ferrule 234 and annular wall 212h, tooth 212i of annular wall 212h of nose 212c is disposed within outer radial groove 342a of outer connector member 342, and stopper or tooth 234b of ferrule 234 is disposed distally of outer connector member 342.

When outer connector member 342 is fully inserted into ferrule 234 and annular wall 212h, the distal end of drive shaft 232 enters into inner connector member 344 such that the at least one longitudinally extending inner rib 344a of inner connector member 344 mechanically engages or meshes with the plurality of axially extending ribs 232a provided at the distal end of drive shaft 232.

With outer connector member 342 fully inserted into ferrule 234 and annular wall 212h, ferrule 234 is rotated from the exchange position to the lock position, whereby stopper or tooth 234b of ferrule 234 is rotated to a radial position, out of alignment with outer radial groove 342a of outer connector member 342, to block withdrawal of outer connector member 342 from within ferrule 234 and from within annular wall 212h of nose 212c of handle housing 212.

As illustrated in FIGS. 20-23, endoscopic assembly 300 includes a shipping wedge, plug or cap 350 configured and adapted for selective connection to connector 340. Cap 350 includes an end wall 352, at least one leg 354 extending from end wall 352 and being configured and dimensioned for selective receipt in a respective longitudinally extending outer radial groove 342a (FIG. 21) of outer connector member 342, and a stem (not shown) extending from end wall 352 and being configured and dimensioned for selective receipt into inner connector member 344 for engagement with longitudinally extending inner rib(s) 344a of inner connector member 344. When cap 350 is secured to connector 340, the at least one leg 354 and the stem of cap 350 engage outer connector member 342 and inner connector member 344 to prevent their rotation relative to one another.

Cap 350 is used to fix the radial position of inner tube 320 relative to outer tube 310 and thus ensure that the stack of surgical anchors 100 are not prematurely advanced through endoscopic assembly 300 prior to connection of endoscopic assembly 300 to handle assembly 210. If the stack of surgical anchors 100 are advanced through endoscopic assembly 300, prior to connection of endoscopic assembly 300 to handle assembly 210, a timing of the firing of tack applier 200 may be effected, whereby each fully stroke of trigger 214 may either not fully fire a surgical anchor 100 from endoscopic assembly 300 or may begin to fire a second surgical anchor 100 from endoscopic assembly 300.

In an operation of surgical tacker 200, as illustrated in FIGS. 26-28, 36 and 37, with endoscopic assembly 300 operatively connected and locked to handle assembly 210, as described above, as drive shaft 232 is rotated due to an actuation of trigger 214, also as described above, said rotation is transmitted to inner tube 320 of endoscopic assembly 300 via the engagement of the plurality of axially extending ribs 232a provided at the distal end of drive shaft 232 with the at least one longitudinally extending inner rib 344a of inner connector member 344.

Again, as inner tube 320 is rotated, about its longitudinal axis, with respect to coil 330, the pair of tines 320$a_1$ of inner tube 320 transmit the rotation to the entire stack of anchors 100 and advance the entire stack of anchors 100 distally, owing to head threads 114a, 114b of anchors 100 engaging with coil 330.

In accordance with the present disclosure, the components of surgical tacker 200, and anchors 100 are dimensioned such that a single complete and full actuation of trigger 214 results in a firing of a singe anchor 100 (i.e., the distal-most anchor of the stack of anchors 100 loaded in endoscopic assembly 300) from endoscopic assembly 300.

Surgical tacker 200 may be repeatedly fired to fire anchors from endoscopic assembly 300 until the surgical procedure is complete or until endoscopic assembly 300 is spent of anchors 100. If endoscopic assembly 300 is spent of anchors 100, and if additional anchors 100 are required to complete the surgical procedure, spent endoscopic assembly 300 may be replaced with a new (i.e., loaded with anchors 100) endoscopic assembly 300. Alternatively, is it is desired to change the types of anchors 100 that are being used in the surgical procedure, non-spent endoscopic assembly 300 (loaded with a first type of anchors 100) may be replaced with another endoscopic assembly 300 (loaded with a second, different type of anchors 100).

As shown in FIGS. 14-19 and 30-33, in order to replace an endoscopic assembly 300 with another endoscopic assembly 300, with trigger 214 in the fully un-actuated position, as described above, the surgeon actuates or rotates ferrule 234 from the locked position (FIGS. 14-19) to the exchange position (FIGS. 30-33) to release the loaded or connected endoscopic assembly 300, decouples or withdraws endoscopic assembly 300 from handle assembly 210, loads or connects a new endoscopic assembly 300 to handle assembly 210, and actuates or rotates ferrule 234 from the exchange position to the locked position to retain the new endoscopic assembly 300 in handle assembly 210.

Following a surgical procedure, ferrule 234 may be removed or disconnected from handle housing 212 such that the ferrule 234 and the remainder of handle assembly 210 may by cleaned by sterilization, washing, wiping, autoclaving, chemical processing and the like. With reference to FIGS. 30-33 and 41-47, in order to disconnect ferrule 234 from handle housing 212, ferrule 234 is rotated from the exchange position (FIGS. 30-33) to the release position (FIGS. 41-44), wherein ferrule 234 is rotated relative to handle housing 212 until radially inwardly extending nubs 234c of ferrule 234 are at the end of a long leg of L-shaped slots 212d of nose 212c of handle housing 212. At this point, ferrule 234 may be axially separated from handle housing 212.

In accordance with the present disclosure, it is contemplated that a plurality of different endoscopic assemblies 300 may be provided, wherein endoscopic assemblies may be available which are loaded with surgical anchors fabricated from different materials (e.g., bioabsorbable, permanent, etc.), or endoscopic assemblies may be available having different lengths (e.g., short, medium, long, etc.) wherein the particular length endoscopic assembly is loaded with a respective number of surgical anchors. Accordingly, depending on the particular surgical procedure (i.e., hernia procedure), the surgeon may select any one or combination of endoscopic assemblies desired or needed, and the surgeon may interchange or exchange endoscopic assemblies as needed or desired during the surgical procedure.

In an embodiment, it is contemplated that all the endoscopic assemblies may have the same length, but be loaded with varying numbers of surgical anchors therein. In this manner, the surgeon may choose an endoscopic assembly loaded with fewer or more surgical anchors depending on the type of surgical procedure to be performed.

In accordance with the present disclosure, it is also contemplated that handle assembly 100 may be replaced by an electromechanical control module configured and adapted to drive the inner tube of anchor retaining/advancing assembly to fire or actuate the surgical device. The electromechanical control module may include at least one microprocessor, at least one drive motor controllable by the at least one microprocessor, and a source of power for energizing the at least one microprocessor and the at least one drive motor.

An embodiment is an endoscopic surgical device, comprising; a handle assembly including a handle housing and a trigger operatively connected to the handle housing, and a drive mechanism actuatable by the trigger; and an endoscopic assembly selectively connectable to the handle assembly, the endoscopic assembly including: an outer tube defining a lumen therethrough; an inner tube rotatably supported in the outer tube and defining a lumen therethrough; a plurality of surgical anchors loaded in the lumen of the inner tube of the endoscopic assembly, wherein each anchor includes a threaded body portion and a head portion acted upon by the inner tube to axially advanced the fire the surgical anchors from the endoscopic assembly; and a connector having: an outer connector member non-rotatably connected to a proximal end of the outer tube and being non-rotatably connectable to the handle assembly; and an inner connector member non-rotatably connected to a proximal end of the inner tube and being non-rotatably connectable to the drive mechanism, wherein the outer connector member and the inner connector member are rotatable with respect to one another. Additionally wherein the handle housing includes a tooth projecting from a surface thereof, and wherein the outer connector member includes a channel formed therein, wherein the channel of the outer connector member receives the tooth of the handle housing when the endoscopic assembly is connected to the handle assembly, wherein the tooth inhibits rotation of the outer connector member when the trigger is actuated to rotate the inner connector member of the endoscopic assembly. Additionally wherein the handle assembly includes a ferrule removably and rotatably connected to the handle housing, the ferrule defining an aperture therein that is in operative alignment with the drive mechanism of the handle assembly, the ferrule including a tooth projecting radially into the aperture of the ferrule, the ferrule having: a first position wherein the tooth of the ferrule is radially aligned with the tooth of the handle housing; and a second position wherein the tooth of the ferrule is radially out of alignment with the tooth of the handle housing. Additionally wherein when the ferrule is in the first position the endoscopic assembly is connectable to and disconnectable from the handle assembly. Additionally wherein the channel of the outer connector member is formed in an outer radial surface thereof and extends axially along an entire length thereof, and wherein during connection of the endoscopic assembly to the handle assembly and disconnection of the endoscopic assembly from the handle assembly, the tooth of the ferrule passes along the channel of the outer connector member. Additionally wherein the outer channel of the outer connector member defines a length, wherein when the endoscopic assembly is connected to the handle assembly, the tooth of the ferrule is disposed distally of the channel of the outer connector member, and wherein the ferrule is rotatable to the second position such that the tooth of the ferrule inhibits disconnection of the endoscopic assembly and handle assembly from one another. Additionally wherein the ferrule is rotatable to a third position wherein the ferrule is disconnectable from the handle housing. Additionally wherein the handle assembly includes a safety lock assembly supported on the handle housing, the safety lock assembly includes a proximal end disposed within the handle housing and being in operative association with the drive mechanism, and a distal end projecting from the handle housing and being in operative association with the ferrule. Additionally wherein: when the ferrule is in the first position, the safety lock assembly is in a first position such that the proximal end of the safety lock assembly engages the drive mechanism to block operation of the drive mechanism; and when the ferrule is in the second position, the safety lock assembly is in a second position such that the proximal end of the safety lock assembly is disengaged from the drive mechanism to permit operation of the drive mechanism. Additionally wherein the ferrule is dimensioned to actuate the safety lock assembly between the first and second positions thereof as the ferrule is moved between respective first and second positions thereof. Additionally wherein the safety lock assembly includes a lock plate supported on and extending radially from the proximal end thereof, wherein the lock plate has a generally pie-shaped profile, wherein the drive mechanism includes a gear defining a slot therein, and wherein the lock plate of the safety lock assembly is disposed within the slot of the gear of the drive mechanism when the ferrule is in the first position. Additionally wherein the drive mechanism includes a plurality of gears, wherein at least one gear is actuated by the trigger, and wherein at least one gear actuates a drive shaft extending from the handle housing, wherein the drive shaft is keyed for selective connection to the inner connector member supported at the proximal end of the inner tube. Additionally wherein the outer tube includes a helical thread disposed within the lumen thereof wherein the inner tube defines a splined distal end, wherein the splined distal end of the inner tube is defined by a pair of opposed longitudinally extending tines and a pair of opposed longitudinally extending channels; and wherein the head portion of each of the plurality of surgical anchors defines a pair of opposed radially outer threads and a pair of opposed radial recesses, wherein the pair of radial recesses of each head portion receives respective tines of the inner tube and wherein the pair of opposed radially outer threads of each head portion projects from the pair of opposed longitudinally extending channels of the inner tube and engage the inner helical thread of the outer tube.

An embodiment is an endoscopic surgical device, comprising; a handle assembly including: a handle housing and a trigger operatively connected to the handle housing, wherein the handle housing includes a tooth projecting from a surface thereof a drive mechanism actuatable by the trigger; and a ferrule removably and rotatably connected to the handle housing, the ferrule defining an aperture therein that is in operative alignment with the drive mechanism of the handle assembly, the ferrule including a tooth projecting radially into the aperture of the ferrule, the ferrule having: a first position wherein the tooth of the ferrule is radially aligned with the tooth of the handle housing; and a second position wherein the tooth of the ferrule is radially out of alignment with the tooth of the handle housing; and an endoscopic assembly extending from the handle assembly, the endoscopic assembly including: an outer tube defining a lumen therethrough and a helical inner coil; an inner tube rotatably supported in the outer tube and defining a lumen therethrough; a plurality of surgical anchors loaded in the lumen of the inner tube of the endoscopic assembly, wherein each anchor includes a threaded body portion and a head portion extending radially beyond the inner tube and engaging the helical inner coil; and a connector having: an outer connector member non-rotatably connected to a proximal end of the outer tube, being insertable through the aperture of the ferrule and being non-rotatably connectable to the handle assembly, wherein the outer connector member defines a channel formed therein that is configured to receive the tooth of the ferrule when the endoscopic assembly is connected to the handle assembly; and an inner connector member non-rotatably connected to a proximal end of the inner tube and being non-rotatably connectable to the drive mechanism, wherein the outer connector member and the inner connector member are rotatable with respect to one another. Additionally wherein the channel of the outer connector member receives the tooth of the handle housing when the endoscopic assembly is connected to the handle assembly, wherein the tooth inhibits rotation of the outer connector member when the trigger is actuated to rotate the inner connector member of the endoscopic assembly. Additionally wherein when the ferrule is in the first position the endoscopic assembly is connectable to and disconnectable from the handle assembly. Additionally wherein the channel of the outer connector member is formed in an outer radial surface thereof and extends axially along an entire length thereof, and wherein during connection of the endoscopic assembly to the handle assembly and disconnection of the endoscopic assembly from the handle assembly, the tooth of the ferrule passes along the channel of the outer connector member. Additionally wherein the outer channel of the outer connector member defines a length, wherein when the endoscopic assembly is connected to the handle assembly, the tooth of the ferrule is disposed distally of the channel of the outer connector member, and wherein the ferrule is rotatable to the second position such that the tooth of the ferrule inhibits disconnection of the endoscopic assembly and handle assembly from one another. Additionally wherein the ferrule is rotatable to a third position wherein the ferrule is disconnectable from the handle housing. Additionally wherein the handle assembly includes a safety lock assembly supported on the handle housing, the safety lock assembly includes a proximal end disposed within the handle housing and being in operative association with the drive mechanism, and a distal end projecting from the handle housing and being in operative association with the ferrule. Additionally wherein: when the ferrule is in the first position, the safety lock assembly is in a first position such that the proximal end of the safety lock assembly engages the drive mechanism to block operation of the drive mechanism; and when the ferrule is in the second position, the safety lock assembly is in a second position such that the proximal end of the safety lock assembly is disengaged from the drive mechanism to permit operation of the drive mechanism. Additionally wherein the ferrule is dimensioned to actuate the safety lock assembly between the first and second positions thereof as the ferrule is moved between respective first and second positions thereof. Additionally wherein the safety lock assembly includes a lock plate supported on and extending radially from the proximal end thereof, wherein the lock plate has a generally pie-shaped profile, wherein the drive mechanism includes a gear defining a slot therein, and wherein the lock plate of the safety lock assembly is disposed within the slot of the gear of the drive mechanism when the ferrule is in the first position. Additionally wherein the drive mechanism includes a plurality of gears, wherein at least one gear is actuated by the trigger, and wherein at least one gear actuates a drive shaft extending from the handle housing, wherein the drive shaft is keyed for selective connection to the inner connector member supported at the proximal end of the inner tube. Additionally wherein the outer tube includes a helical thread disposed within the lumen thereof; wherein the inner tube defines a splined distal end, wherein the splined distal end of the inner tube is defined by a pair of opposed longitudinally extending tines and a pair of opposed longitudinally extending channels; and wherein the head portion of each of the plurality of surgical anchors defines a pair of opposed radially outer threads and a pair of opposed radial recesses, wherein the pair of radial recesses of each head portion receives respective tines of the inner tube and wherein the pair of opposed radially outer threads of each head portion projects from the pair of opposed longitudinally extending channels of the inner tube and engage the inner helical thread of the outer tube.

An embodiment is an endoscopic surgical device, comprising; a handle assembly including: a handle housing and a trigger operatively connected to the handle housing, wherein the handle housing includes a tooth projecting from a surface thereof; a drive mechanism actuatable by the trigger; a ferrule removably and rotatably connected to the handle housing, the ferrule defining an aperture therein that is in operative alignment with the drive mechanism of the handle assembly, the ferrule including a tooth projecting radially into the aperture of the ferrule, the ferrule having: a first position wherein the tooth of the ferrule is radially aligned with the tooth of the handle housing; and a second position wherein the tooth of the ferrule is radially out of alignment with the tooth of the handle housing; and a safety lock assembly supported on the handle housing, the safety lock assembly includes a proximal end disposed within the handle housing and being in operative association with the drive mechanism, and a distal end projecting from the handle housing and being in operative association with the ferrule; when the ferrule is in the first position, the safety lock assembly is in a first position such that the proximal end of the safety lock assembly engages the drive mechanism to block operation of the drive mechanism; and when the ferrule is in the second position, the safety lock assembly is in a second position such that the proximal end of the safety lock assembly is disengaged from the drive mechanism to permit operation of the drive mechanism. Additionally wherein the ferrule is dimensioned to actuate the safety lock assembly between the first and second positions thereof as the ferrule is moved between respective first and second positions thereof. Additionally wherein the safety lock assembly includes a lock plate supported on and extending radially from the proximal end thereof, wherein the lock plate has a generally pie-shaped profile, wherein the drive mechanism includes a gear defining a slot therein, and wherein the lock plate of the safety lock assembly is disposed within the slot of the gear of the drive mechanism when the ferrule is in the first position. Additionally further comprising: an endoscopic assembly extending from the handle assembly, the endoscopic assembly including: an outer tube defining a lumen therethrough and a helical inner coil; an inner tube rotatably supported in the outer tube and defining a lumen therethrough; a plurality of surgical anchors loaded in the lumen of the inner tube of the endoscopic assembly, wherein each anchor includes a threaded body portion and a head portion extending radially beyond the inner tube and engaging the helical inner coil; and a connector having: an outer connector member non-rotatably connected to a proximal end of the outer tube, and being insertable through the aperture of the ferrule and being non-rotatably connectable to the handle assembly, wherein the outer connector member defines a channel formed therein that is configured to receive the tooth of the ferrule and the tooth of the handle housing when the endoscopic assembly is connected to the handle assembly; and an inner connector member non-rotatably connected to a proximal end of the inner tube and being non-rotatably connectable to the drive mechanism, wherein the outer connector member and the inner connector member are rotatable with respect to one another. Additionally wherein the drive mechanism includes a plurality of gears, wherein at least one gear is actuated by the trigger, and wherein at least one gear actuates a drive shaft extending from the handle housing, wherein the drive shaft is keyed for selective connection to the inner connector member supported at the proximal end of the inner tube. Additionally wherein the outer tube includes a helical thread disposed within the lumen thereof; wherein the inner tube defines a splined distal end, wherein the splined distal end of the inner tube is defined by a pair of opposed longitudinally extending tines and a pair of opposed longitudinally extending channels; and wherein the head portion of each of the plurality of surgical anchors defines a pair of opposed radially outer threads and a pair of opposed radial recesses, wherein the pair of radial recesses of each head portion receives respective tines of the inner tube and wherein the pair of opposed radially outer threads of each head portion projects from the pair of opposed longitudinally extending channels of the inner tube and engage the inner helical thread of the outer tube.

It will be understood that various modifications may be made to the embodiments disclosed herein. For example, the length of the linear row of staples or fasteners may be modified to meet the requirements of a particular surgical procedure. Thus, the length of the linear row of staples and/or fasteners within a staple cartridge assembly may be varied accordingly. Therefore, the above description should not be construed as limiting, but merely as exemplifications of various embodiments. Those skilled in the art will envision other modifications within the scope and spirit of the claims appended thereto.

What is claimed is:

1. An endoscopic surgical device, comprising;
a handle assembly including a handle housing and a trigger operatively connected to the handle housing, and a drive mechanism actuatable by the trigger, wherein the handle housing includes a tooth projecting from a surface thereof, wherein the handle assembly includes a ferrule removably and rotatably connected to the handle housing, the ferrule defining an aperture therein that is in operative alignment with the drive mechanism of the handle assembly, the ferrule including a tooth projecting radially into the aperture of the ferrule, the ferrule having:
   a first position wherein the tooth of the ferrule is radially aligned with the tooth of the handle housing; and
   a second position wherein the tooth of the ferrule is radially out of alignment with the tooth of the handle housing; and
an endoscopic assembly selectively connectable to the handle assembly, the endoscopic assembly including:
   an outer tube defining a lumen therethrough and having an outer helical thread disposed within the lumen thereof, the outer tube defining a proximal end and a distal end;
   an inner tube rotatably supported in the outer tube, the inner tube defining a lumen therethrough and having a proximal end and a splined distal end, wherein the splined distal end of the inner tube is defined by a pair of opposed longitudinally extending tines and a pair of opposed longitudinally extending channels;
   a plurality of surgical anchors loaded in the lumen of the inner tube of the endoscopic assembly, wherein each anchor of the plurality of surgical anchors includes a threaded body portion, and a head portion defining a pair of opposed radially outer threads and a pair of opposed radial recesses, wherein the pair of radial recesses of each head portion receives a respective tine of the pair of opposed longitudinally extending channel of the inner tube and wherein the pair of opposed radially outer threads of each head portion projects from the pair of opposed longitudinally extending channels of the inner tube and engage the inner helical thread of the outer tube; and
   a connector having:
      an outer connector member non-rotatably connected to the proximal end of the outer tube and being non-rotatably connectable to the handle assembly, the outer connector member including a channel formed therein, wherein:
         the channel of the outer connector member receives the tooth of the handle housing when the endoscopic assembly is connected to the handle assembly; and
         the tooth inhibits rotation of the outer connector member when the trigger is actuated to rotate the inner connector member of the endoscopic assembly; and
      an inner connector member non-rotatably connected to the proximal end of the inner tube and being non-rotatably connectable to the drive mechanism, wherein the outer connector member and the inner connector member are rotatable with respect to one another.

2. The endoscopic surgical device according to claim 1, wherein when the ferrule is in the second position the endoscopic assembly is connectable to and disconnectable from the handle assembly.

3. The endoscopic surgical device according to claim 2, wherein the channel of the outer connector member is formed in an outer radial surface thereof and extends axially along an entire length thereof, and
   wherein during connection of the endoscopic assembly to the handle assembly and disconnection of the endoscopic assembly from the handle assembly, the tooth of the ferrule passes along the channel of the outer connector member.

4. The endoscopic surgical device according to claim 3, wherein the outer channel of the outer connector member defines a length, wherein when the endoscopic assembly is connected to the handle assembly, the tooth of the ferrule is disposed outside of the channel of the outer connector member, and wherein the ferrule is rotatable to the first position such that the tooth of the ferrule inhibits disconnection of the endoscopic assembly and handle assembly from one another.

5. The endoscopic surgical device according to claim 1, wherein the ferrule is rotatable to a third position wherein the ferrule is disconnectable from the handle housing.

6. The endoscopic surgical device according to claim 1, wherein the handle assembly includes a safety lock assembly supported on the handle housing, the safety lock assembly includes a proximal end disposed within the handle housing and being in operative association with the drive mechanism, and a distal end projecting from the handle housing and being in operative association with the ferrule.

7. The endoscopic surgical device according to claim 6, wherein:
   when the ferrule is in the first position, the safety lock assembly is in a first position such that the proximal end of the safety lock assembly engages the drive mechanism to block operation of the drive mechanism; and
   when the ferrule is in the second position, the safety lock assembly is in a second position such that the proximal end of the safety lock assembly is disengaged from the drive mechanism to permit operation of the drive mechanism.

8. The endoscopic surgical device according to claim 7, wherein the ferrule is dimensioned to actuate the safety lock assembly between the first and second positions thereof as the ferrule is moved between respective first and second positions thereof.

9. The endoscopic surgical device according to claim 7, wherein the safety lock assembly includes a lock plate supported on and extending radially from the proximal end thereof, wherein the drive mechanism includes a gear defining a slot therein, and
   wherein the lock plate of the safety lock assembly is disposed within the slot of the gear of the drive mechanism when the ferrule is in the first position.

10. The endoscopic surgical device according to claim 9, wherein the drive mechanism includes a plurality of gears, wherein at least one gear is actuated by the trigger, and wherein at least one gear actuates a drive shaft extending from the handle housing, wherein the drive shaft is keyed for selective connection to the inner connector member supported at the proximal end of the inner tube.

* * * * *